US007090834B1

(12) United States Patent
Cunningham et al.

(10) Patent No.: US 7,090,834 B1
(45) Date of Patent: Aug. 15, 2006

(54) VASCULAR ENDOTHELIAL CELL GROWTH FACTOR VARIANTS AND USES THEREOF

(75) Inventors: Brian C. Cunningham, San Mateo, CA (US); Abraham M. de Vos, Oakland, CA (US); Bing Li, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/546,857

(22) Filed: Apr. 10, 2000

Related U.S. Application Data

(60) Provisional application No. 60/184,235, filed on Feb. 23, 2000, provisional application No. 60/129,788, filed on Apr. 16, 1999.

(51) Int. Cl.
C12N 15/16 (2006.01)
A61K 38/18 (2006.01)
C07H 21/04 (2006.01)

(52) U.S. Cl. ............... 424/85.1; 435/7.1; 435/7.2; 435/69.1; 435/69.4; 435/325; 435/252.3; 435/254.11; 435/320.1; 530/399; 436/501; 536/23.5; 536/23.51; 930/120

(58) Field of Classification Search ............... 424/85.1, 424/198.1; 435/69.1, 69.4, 69.5, 440, 325, 435/252.3, 320.1, 7.1, 7.2, 254.11; 436/501; 530/350, 351, 399; 536/23.1, 23.5, 23.51; 930/120
See application file for complete search history.

(56) References Cited

U.S. PATENT DOCUMENTS 6,020,473 A * 2/2000 Keyt et al.
2002/0169292 A1 * 11/2002 Weintraub et al.

FOREIGN PATENT DOCUMENTS

WO WO 90/13649 11/1990
WO WO 97/08313 3/1997
WO WO 98/16551 4/1998

OTHER PUBLICATIONS

Y.A.-Muller et al., "VEGF and the Fab fragment of a humanized neutralizing antibody: crystal structure of the complex at 2.4 A resolution and mutational analysis of the interface" Structure 6:1153-1167, Sep. 15, 1998.*
G. Siemeister et al., "The α-helical domain near the amino terminus is essential for dimerization of vascular endothelial growth factor", J. Biol. Chem. 273(18):11115-11120, May 1, 1998.*
Burgess and Maciag, "The Heparin-Binding (Fibroblast) Growth Factor Family of Proteins" *Annu. Rev. Biochem.* 58:575-606 (1989).
Cao et al., "Heterodimers of placenta growth factor/vascular endothelial growth factor. Endothelial activity, tumor cell expression, and high affinity binding to Flk-1/KDR" *Journal of Biological Chemistry* 271(6):3154-3162 (Feb. 9, 1996).

Cunningham et al., "Interactions of FLT-1 and KDR with phospholipase C γ: Identification of the phosphotyrosine binding sites" *Biochemical & Biophysical Research Communications* 240(3):635-639 (Nov. 26, 1997).
Dougher and Terman, "Autophosphorylation of KDR in the kinase domain is required for maximal VEGF-stimulated kinase activity and reception internalization" *Oncogene* 18(8):1619-1627 (Feb. 25, 1999).
Ferrara et al., "Pituitary Follicular Cells Secrete a Novel Heparin-binding Growth Factor Specific for Vascular Endothelial Cells" *Biochem. & Biophys. Res. Comm.* 161(2):851-858 (Jun. 15, 1989).
Ferrara et al., "The biology of vascular endothelial growth factor" *Endocrine Reviews* 18(1):4-25 (Feb. 1997).
Ferrara, N., "Vascular endothelial growth factor. The trigger for neovascularization in the eye" *Laboratory Investigation* 72(6):615-618 (1995).
Fuh et al., "Requirements for binding and signaling of the kinase domain receptor for vascular endothelial growth factor" *Journal of Biological Chemistry* 273(18):11197-11204 (May 1, 1998).
Gerber et al., "Vascular endothelial growth factor regulates endothelial cell survival through the phosphatidylinositol 3'-kinase/Akt signal transduction pathway. Requirement for Flk-1/KDR activation" *Journal of Biological Chemistry* 273(46):30336-30343 (Nov. 13, 1998).
Ishikawa et al., "Identification of angiogenic activity and the cloning and expression of platelet-derived endothelial cell growth factor" *Nature* 338:357-362 (1989).
Ito et al., "Identification of vascular endothelial growth factor receptor-1 tyrosine phosphorylation sites and binding of SH2 domain-containing molecules" *Journal of Biological Chemistry* 273(36):23410-23418 (Sep. 4, 1998).
Jin et al., "Novel analog of atrial natriuretic peptide selective for receptor-A produces increased diuresis and natriuresis in rats" *Journal of Clinical Investigation* 98(4):969-976 (Aug. 15, 1996).
Keyt et al., "Identification of Vascular Endothelial Growth Factor Determinants for Binding KDR and FLT-1 Receptors: Generation of receptor-selective VEGF variants by site-directed mutagenesis" *Journal of Biological Chemistry* 271(10):5638-5646 (1996).
Keyt et al., "The Carboxyl-terminal Domain (111-165) of Vascular Endothelial Growth Factor Is Critical for Its Mitogenic Potency" *Journal of Biological Chemistry* 271(13):7788-7795 (Mar. 29, 1996).
Kunkel et al., "Efficient site-directed mutagenesis using uracil-containing DNA" *Methods in Enzymology* 204:125-139 (1991).

(Continued)

Primary Examiner—Lorraine Spector
(74) Attorney, Agent, or Firm—Merchant & Gould, P.C.

(57) ABSTRACT

The present invention provides VEGF variants having one or more amino acid mutations in the KDR and/or FLT-1 receptor binding domains in the native VEGF sequence and selective binding affinity for either the KDR receptor or the FLT-1 receptor. Methods of making the VEGF variants and methods of using the VEGF variants are also provided.

55 Claims, 12 Drawing Sheets

OTHER PUBLICATIONS

Landgren et al., "Placenta growth factor stimulates MAP kinase and mitogenicity but not phospholipase C-γ and migration of endothelial cells expressing Flt 1" *Oncogene* 16(3):359-367 (Jan. 22, 1998).

Leung et al., "Vascular Endothelial Growth Factor is a Secreted Angiogenic Mitogen" *Science* 246:1306-1309 (Dec. 1989).

Maglione et al., "Isolation of a human placenta cDNA coding for a protein related to the vascular permeability factor" *Proc. Natl. Acad. Sci.* 88:9267-9271 (1991).

Malavaud et al., "Activation of Flk-1/KDR mediates angiogenesis but not hypotension" *Cardiovascular Research* 36(2):276-281 (Nov. 1997).

Marte and Downward, "PKB/Akt: connecting phosphoinositide 3-kinase to cell survival and beyond" *Trends in Biochemical Sciences* 22(9):355-358 (Sep. 1997).

Meyer et al., "A novel vascular endothelial growth factor encoded by Orf virus, VEGF-E, mediates angiogenesis via signalling through VEGFR-2 (KDR) but not VEGFR-1 (Flt-1) receptor tyrosine kinases" *EMBO Journal* 18(2):363-374 (Jan. 15, 1999).

Muller et al., "The crystal structure of vascular endothelial growth factor (VEGF) refined to 1.93 A resolution: multiple copy flexibility and receptor binding" *Structure* 5(10):1325-1338 (Oct. 15, 1997).

Muller et al., "Vascular endothelial growth factor: crystal structure and functional mapping of the kinase domain receptor binding site" *Proc. Natl. Acad. Sci. USA* 94(14):7192-7197 (Jul. 8, 1997).

Muller et al., "VEGF and the Fab fragment of a humanized neutralizing antibody: crystal structure of the complex at 2.4 A resolution and mutational analysis of the interface" *Structure* 6(9):1153-1167 (Sep. 15, 1998).

Ogawa et al., "A novel type of vascular endothelial growth factor, VEGF-E (NZ-7 VEGF), preferentially utilizes KDR/Flk-1 receptor and carries a potent mitotic activity without heparin-binding domain" *Journal of Biological Chemistry* 273(47):31273-31282 (Nov. 20, 1998).

Olofsson et al., "Vascular endothelial growth factor B (VEGF-B) binds to VEGF receptor-1 and regulates plasminogen activator activity in endothelial cells" *Proc. Natl. Acad. Sci. USA* 95(20):11709-11714 (Sep. 29, 1998).

Park et al., "Placenta growth factor. Potentiation of vascular endothelial growth factor bioactivity, in vitro and in vivo, and high affinity binding to Flt-1 but not to Flk-1/KDR" *Journal of Biological Chemistry* 269(41):25646-15654 (1994).

Polverini et al., "Assay and purification of naturally occurring inhibitor of angiogenesis" *Methods in Enzymology* 198:440-450 (1991).

Rousseau et al., "p38 MAP kinase activation by vascular endothelial growth factor mediates actin reorganization and cell migration in human endothelial cells" *Oncogene* 15(18):2169-2177 (Oct. 1997).

Sawano et al., "Flt-1 but not KDR/Flk-1 tyrosine kinase is a receptor for placenta growth factor, which is related to vascular endothelial growth factor" *Cell Growth & Differentiation* 7(2):213-221 (Feb. 1996).

Sawano et al., "The phosphorylated 1169-tyrosine containing region of flt-1 kinase (VEGFR-1) is a major binding site for PLCγ" *Biochemical & Biophysical Research Communications* 238(2):487-491 (Sep. 18, 1997).

Seetharam et al., "A unique signal transduction from FLT tyrosine kinase, a receptor for vascular endothelial growth factor VEGF" *Oncogene* 10(1):135-147 (Jan. 5, 1995).

Tischer et al., "Vascular endothelial growth factor: a new member of the platelet-derived growth factor gene family" *Biochem. & Biophys. Res. Comm.* 165:1198-1206 (1989).

Waltenberger et al., "Different signal transduction properties of KDR and Flt1, two receptors for vascular endothelial growth factor" *Journal of Biological Chemistry* 269(43):26988-26995 (Oct. 28, 1994).

Walter et al., "The in vivo bioactivity of vascular endothelial growth factor/vascular permeability factor is independant of N-linked glycosylation" *Laboratory Investigation* 74(2):546-556 (Feb. 1996).

Wang and Keiser, "Vascular endothelial growth factor upregulates the expression of matrix metalloproteinases in vascular smooth muscle cells: role of flt-1" *Circulation Research* 83(8):832-840 (Oct. 19, 1998).

Wells, "Systematic Mutational Analyses of Protein-Protein Interfaces" *Methods in Enzymology* 202:390-411 (1991).

Wennstrom et al., "Activation of phosphoinositide 3-kinase is required for PDGF-stimulated membrane ruffling" *Current Biology* 4(5):385-393 (May 1, 1994).

Weismann et al., "Crystal structure at 1.7 A resolution of VEGF in a complex with domain 2 of the Flt-1 receptor" *Cell* 91(5):695-704 (Nov. 28, 1997).

Wise et al., "Vascular endothelial growth factor (VEGF)-like protein from orf virus NZ2 binds to VEGFR2 and neuropilin-1" *Proc. Natl. Acad. Sci. USA* 96(6):3071-3076 (Mar. 16, 1999).

Yu and Sato, "MAP kinases, phosphatidylinositol 3-kinase, and p70 S6 kinase mediate the mitogenic response of human endothelial cells to vascular endothelial growth factor" *Journal of Cellular Physiology* 178(2):235-246 (Feb. 1999).

* cited by examiner

```
  1   CAGTGTGCTG GCGGCCCGGC GCGAGCCGGC CCGGCCCCGG TCGGGCCTCC
-26

GAAACC  ATG AAC TTT CTG CTG TCT TGG GTG CAT TGG AGC
              M   V   F   L   L   S   W   V   H   W   S
              -26                     -20

90   CTC GCC TTG CTG CTC TAC CTC CAC CAT GCC AAG TGG TCC CAG
-15   L   A   L   L   L   Y   L   H   H   A   K   W   S   Q
                          -10

GCT|GCA CCC ATG GCA GAA GGA GGA GGG CAG AAT CAT CAC
      A  |A → P   M   A   E   G   G   G   Q   N   H   H
      -1  +1                 +5                 +10

171   GAA GTG GTG AAG TTC ATG GAT GTC TAT CAG CGC AGC TAC TGC
 13   E   V   V   K   F   M   D   V   Y   Q   R   S   Y   C
              +15                 +20                 +25

CAT CCA ATC GAG ACC CTG GTG GAC ATC TTC CAG GAG TAC
      H   P   I   E   T   L   V   D   I   F   Q   E   Y
                  +30                 +35

252   CCT GAT GAG ATC GAG TAC ATC TTC AAG CCA TCC TGT GTG CCC
 40   P   D   E   I   E   Y   I   F   K   P   S   C   V   P
      +40                 +45                 +50

CTG ATG CGA TGC GGG GGC TGC TGC AAT GAC GAG GGC CTG
      L   M   R   C   G   G   C   C   N   D   E   G   L
      +55                 +60                 +65

333   GAG TGT GTG CCC ACT GAG GAG TCC AAC ATC ACC ATG CAG ATT
 67   E   C   V   P   T   E   E   S   N   I   T   M   Q   I
                  +70                 +75                 +80

ATG CGG ATC AAA CCT CAC CAA GGC CAG CAC ATA GGA GAG
      M   R   I   K   P   H   Q   G   Q   H   I   G   E
                      +85                 +90

414   ATG AGC TTC CTA CAG CAC AAC AAA TGT GAA TGC AGA CCA AAG
 94   M   S   F   L   Q   H   N   K   C   E   C   R   P   K
          +95                 +100                +105

AAA GAT AGA CCA AGA CAA GAA AAT CCC TGT GGG CCT TGC
      K   D   R   A   R   Q   E   N   P   C   G   P   C
              +110                +115                +120

495   TCA GAG CGG AGA AAG CAT TTG TTT GTA CAA GAT CCG CAG ACG
121   S   E   R   R   K   H   L   F   V   Q   D   P   Q   T
                      +125                +130

TGT AAA TGT TCC TGC AAA AAC ACA GAC TCG CGT TGC AAG
      C   K   C   S   C   K   N   T   D   S   R   C   K
      +135                +140                +145
```

FIG._1A

```
576  GCG AGG CAG CTT GAG TTA AAC GAA CGT ACT TGC AGA TGT GAC
148   A   R   Q   L   E   L   N   E   R   T   C   R   C   D
             +150                +155                +160

AAG CCG AGG CGG TGA GCCGGGCA GGAGGAAGGA GCCTCCCTCA
      K   P   R   R   0
                 +165

661  GGGTTTCGGG AACCAGATCT CTCACCAGGA AAGACTGATA CAGAACGATC

GATACAGAAA CCACGCTGCC GCCACCACAC CATCACCATC GACAGAACAG

761  TCCTTAATCC AGAAACCTGA AATGAAGGAA GAGGAGACTC TGCGCAGAGC

ACTTTGGGTC CGGAGGGCGA GACTCCGGCG GAAGCATTCC CGGGCGGGTG

861  ACCCAGCACG GTCCCTCTTG GAATTGGATT CGCCATTTTA TTTTTCTTGC

TGCTAAATCA CCGAGCCCGG AAGATTAGAG AGTTTTATTT CTGGGATTCC

961  TGTAGACACA CCGCGGCCGC CAGCACACTG
```

FIG._1B

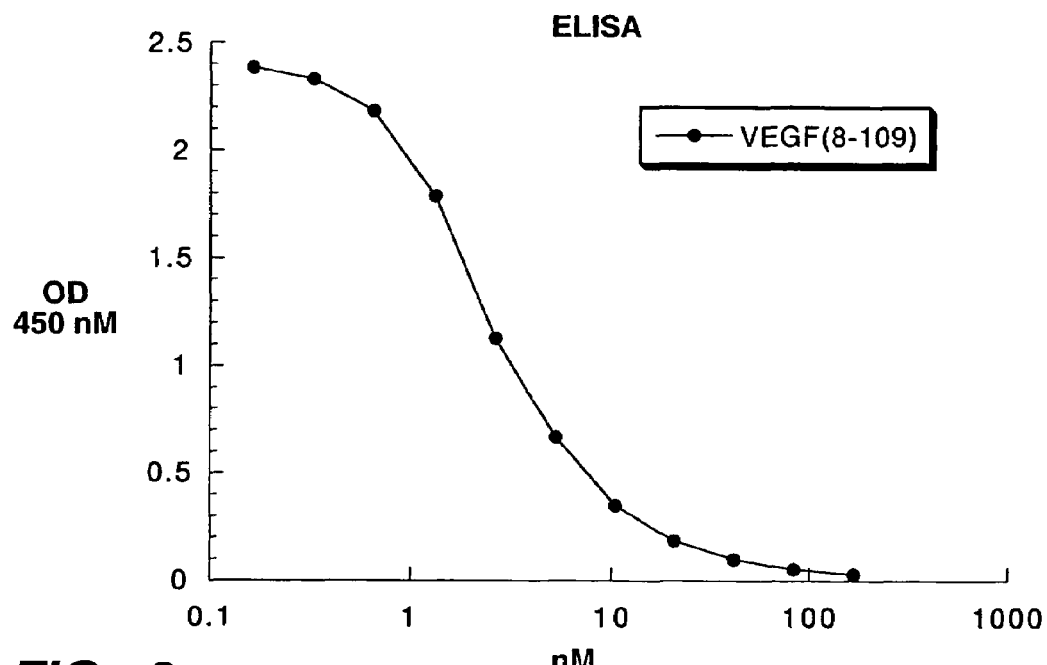
FIG._2
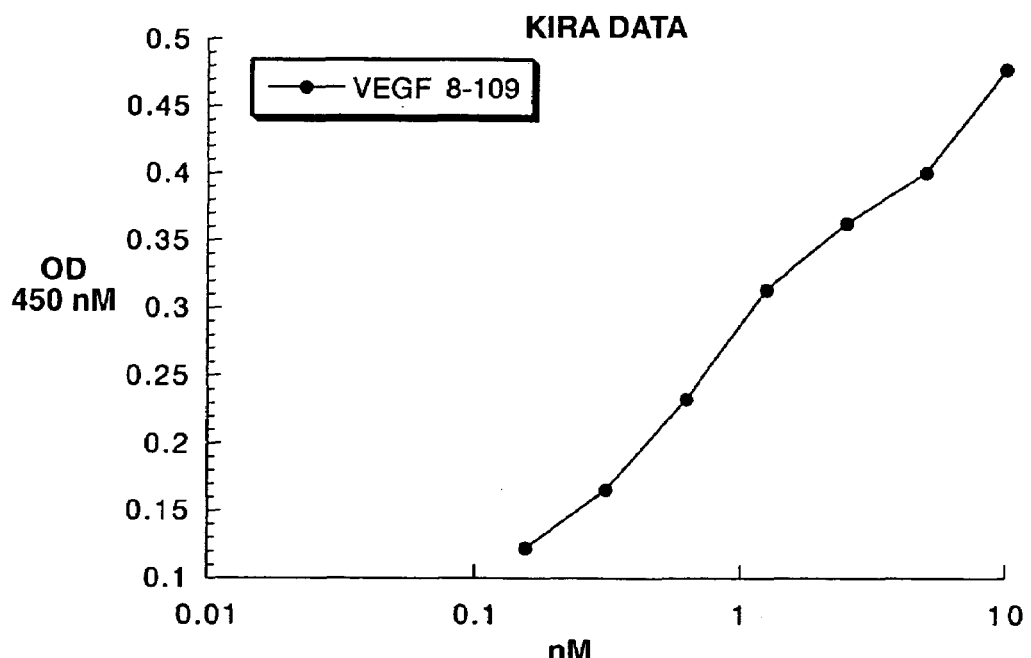
FIG._3

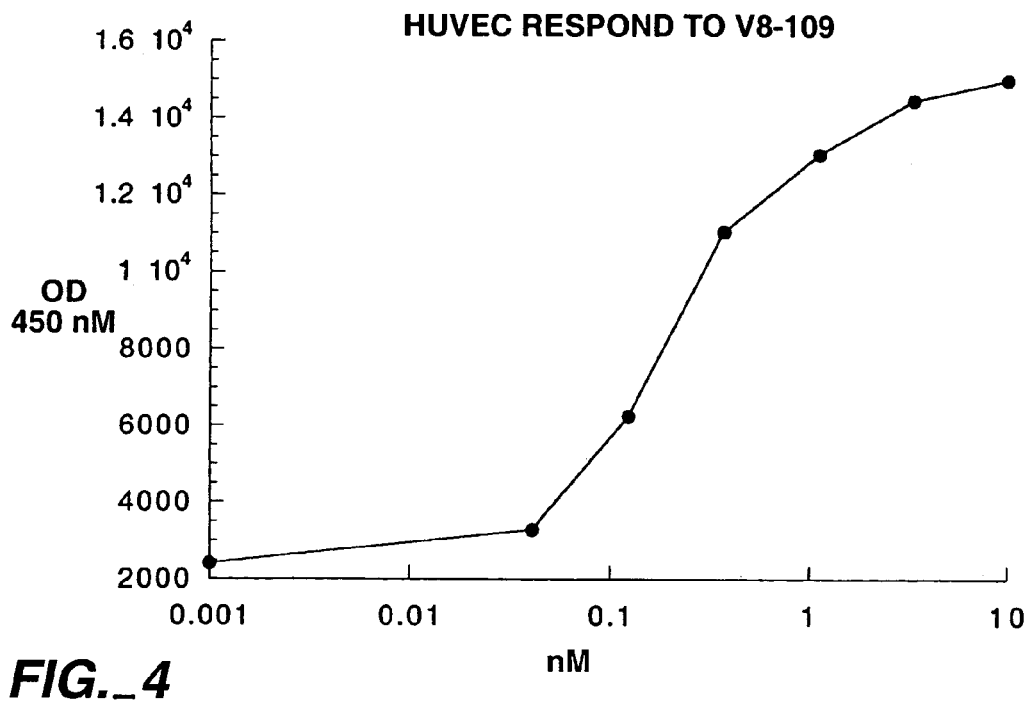
FIG._4
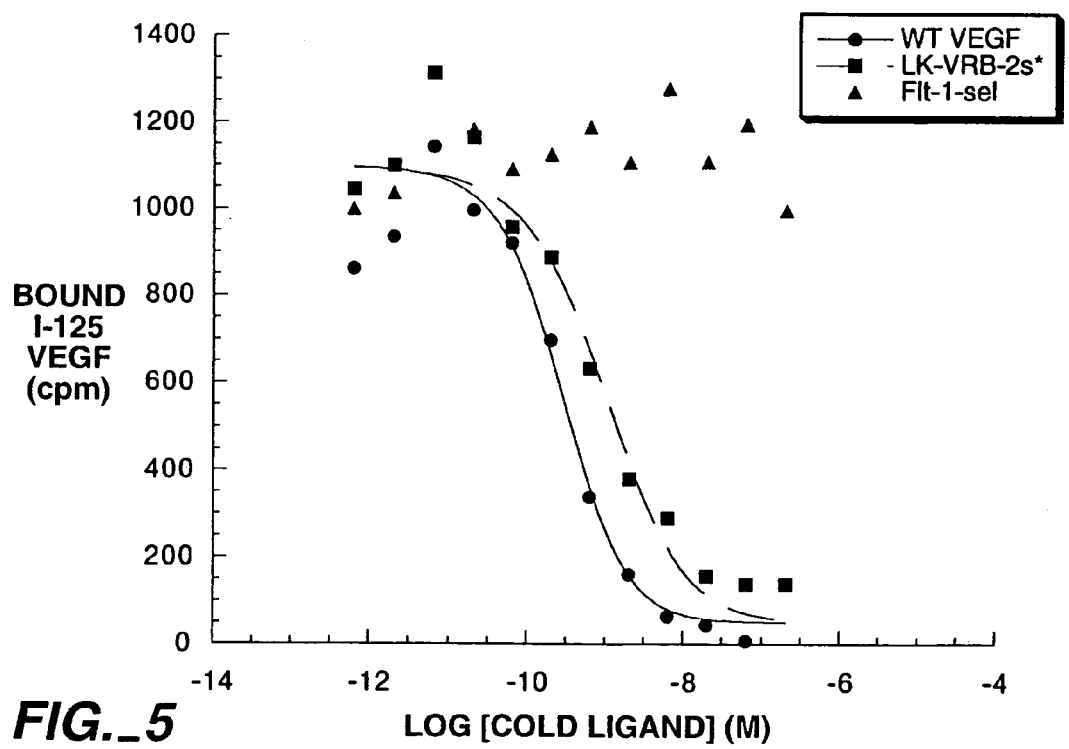
FIG._5

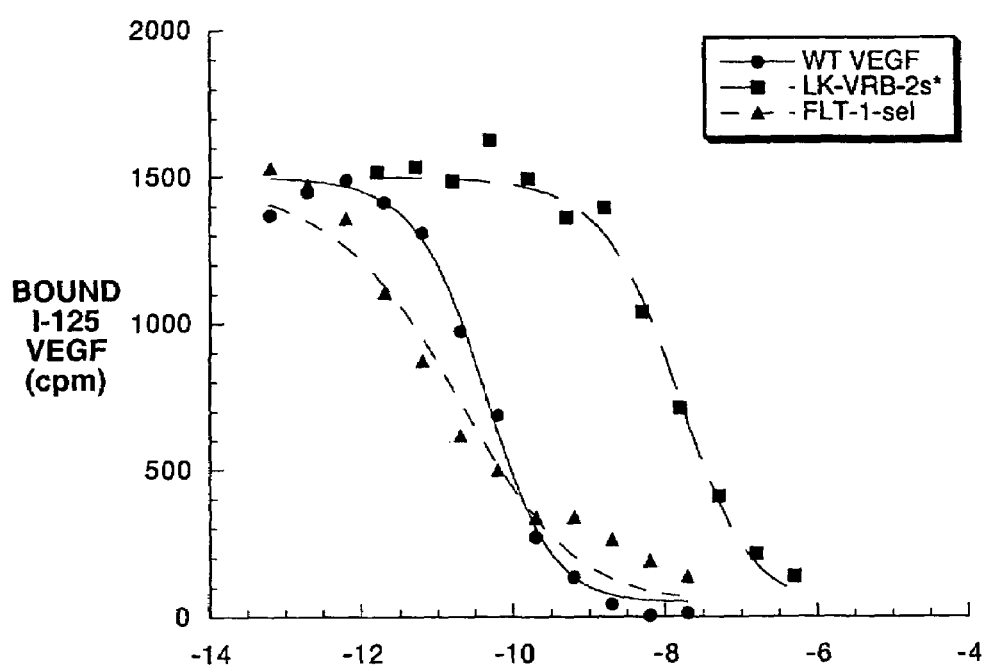
FIG._6

FOLD REDUCTION IN BINDING OF VEGF ALANINE MUTANTS

| RESIDUE | KDR(1-3) | Flt(1-3) |
|---|---|---|
| VEGF(1-109) | 1 (10nM) | 1 (6 nM) |
| 20s Helix: | | |
| Lys 16 | 1 | 1 |
| Phe 17* | 45 | 34 |
| Met 18** | 5 | 9 |
| Tyr 21** | 19 | 29 |
| Gln 22** | 6 | 15 |
| Tyr 25** | 6 | 7 |
| 40s Loop: | | |
| Ile 43* | 21 | 3 |
| Ile 46* | 96 | 4 |
| Phe 47** | 5 | 3 |
| Lys 48** | 1 | 1 |
| 60s Loop: | | |
| Asp 63** | 1 | 8 |
| Glu 64* | 10 | 5 |
| Gly 65** | 1 | 1 |
| Leu 66** | 1 | 10 |
| 80s Loop: | | |
| Gln 79* | 55 | 3 |
| Met 81** | 9 | 5 |
| Ile 83* | 89 | 7 |
| His 86** | 2 | 1 |
| Gln 89 | 1 | 1 |
| Ile 91 | 1 | 1 |
| 100s Loop: | | |
| Lys 101 | 1 | 1 |
| Glu 103 | 1 | 1 |
| Arg 105 | 1 | 1 |
| Pro 106 | 1 | 1 |

FIG._7

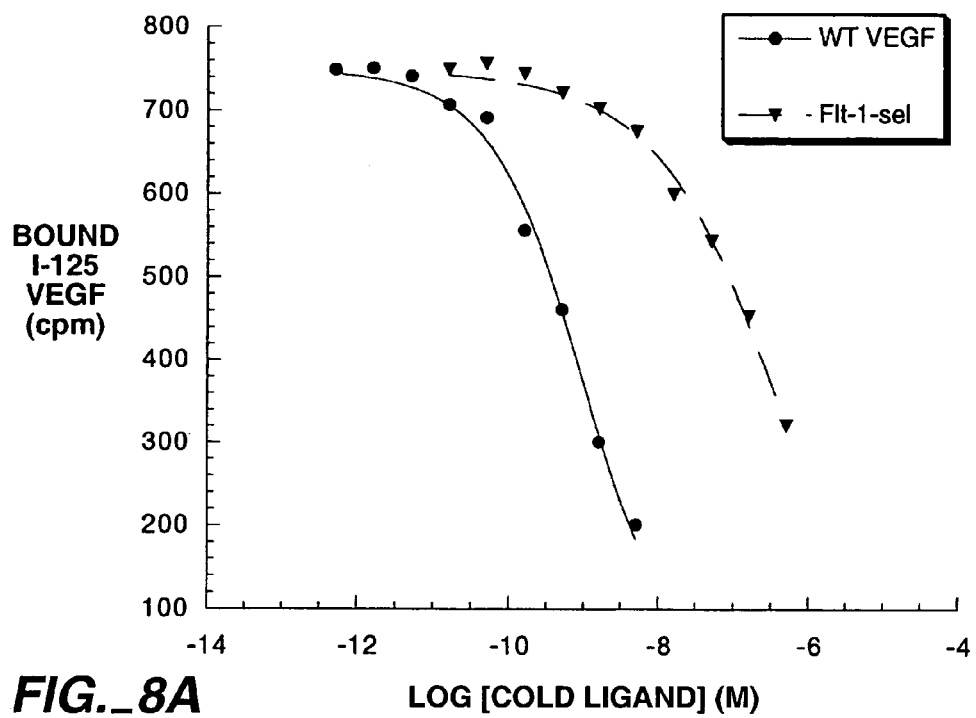
FIG._8A
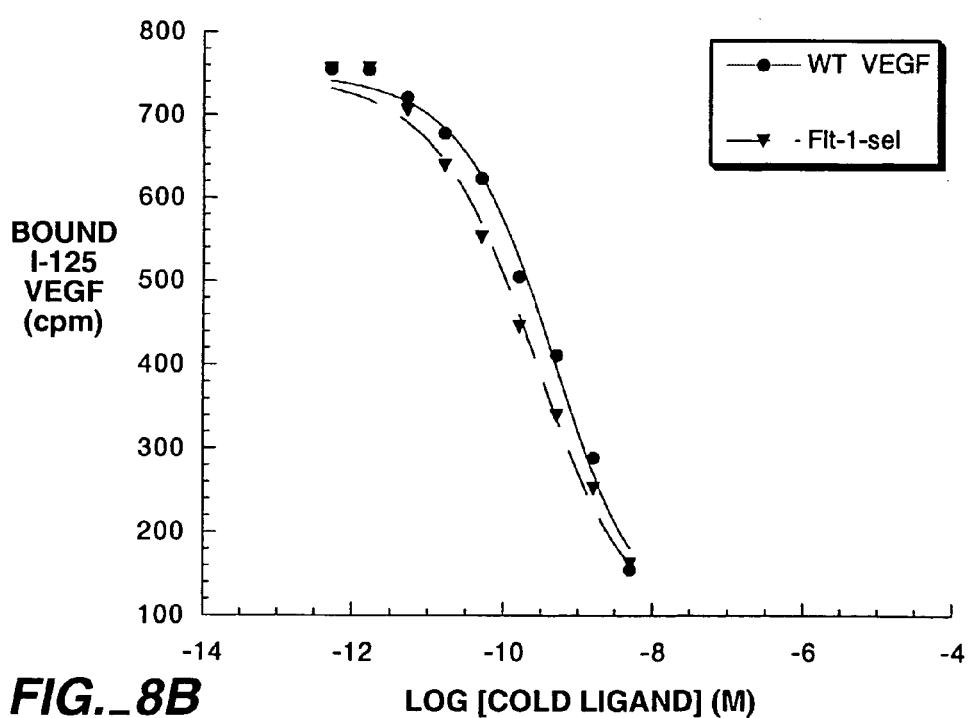
FIG._8B

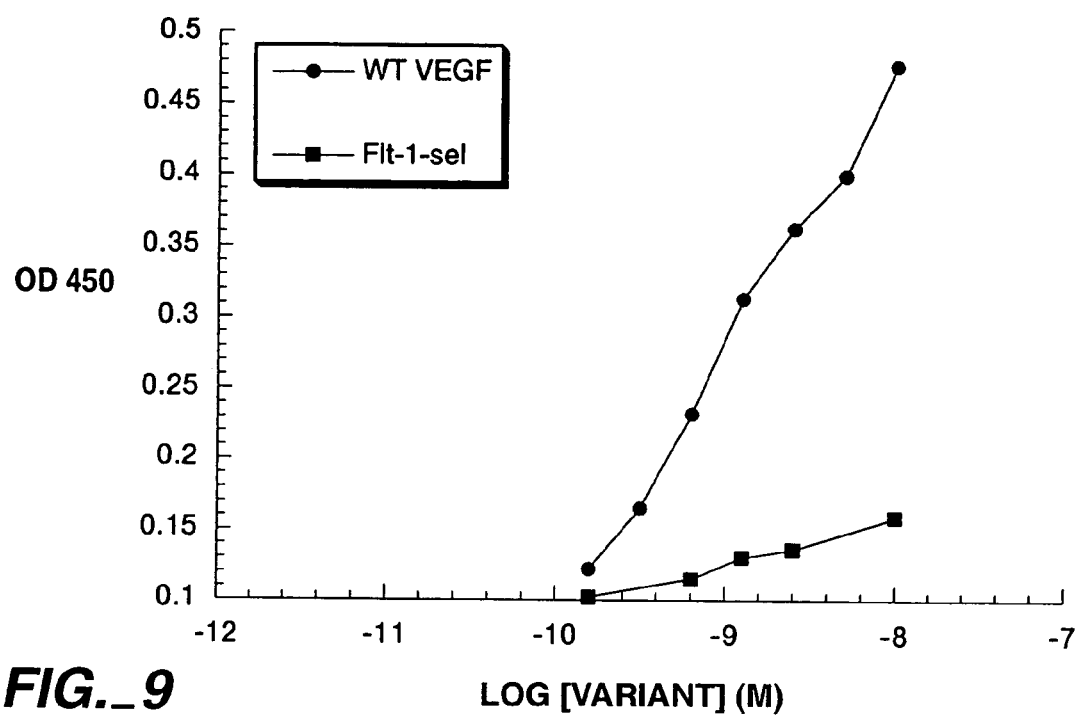
FIG._9
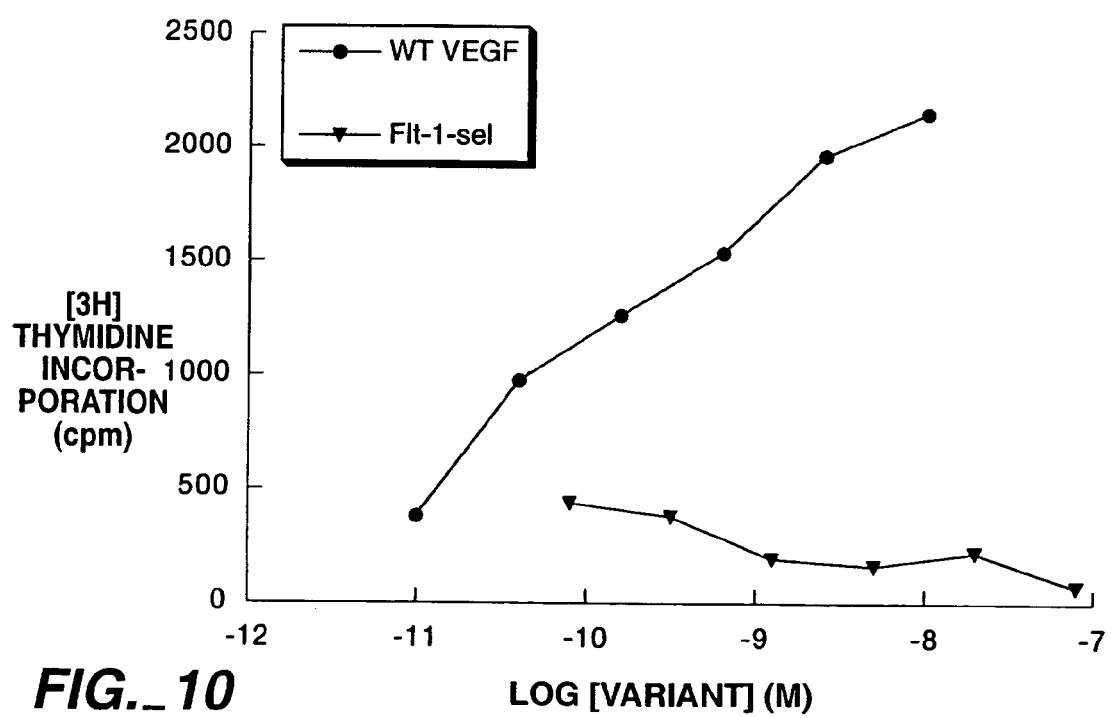
FIG._10

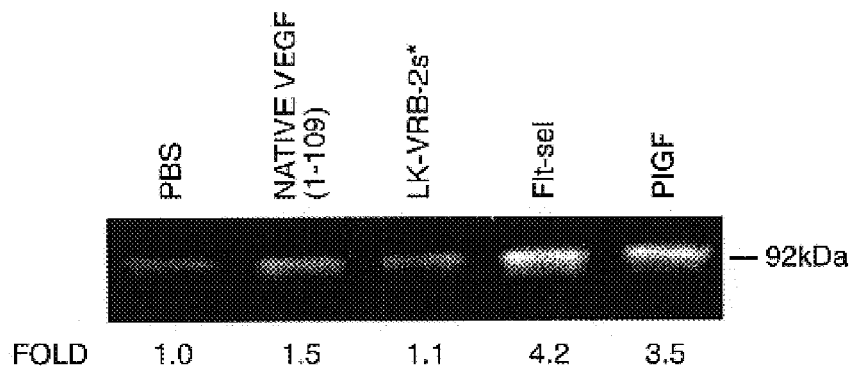
FIG._11
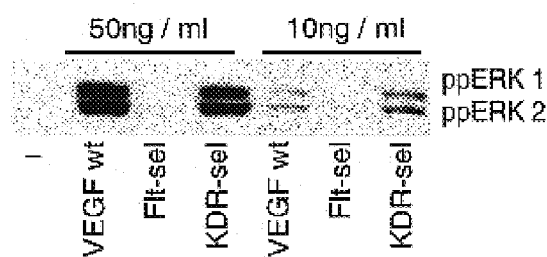
FIG._12A
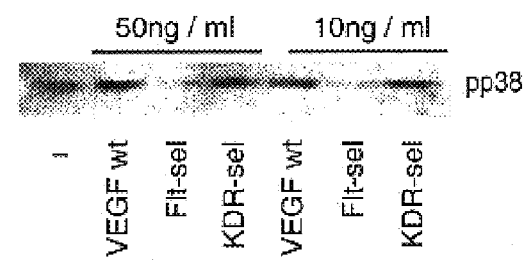
FIG._12B
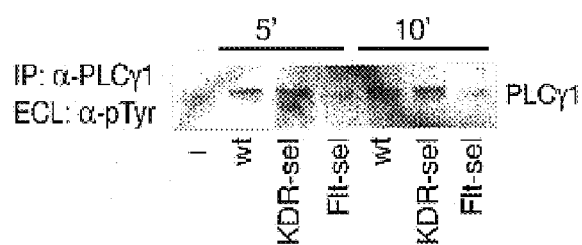
FIG._13A
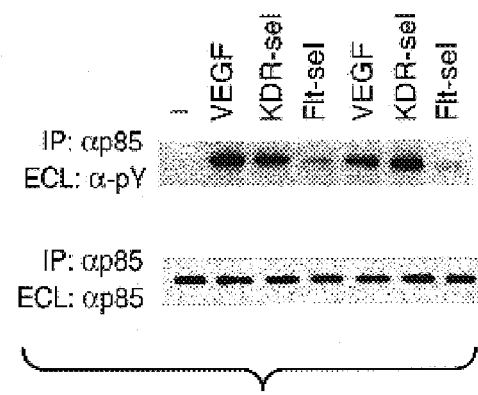
FIG._13B

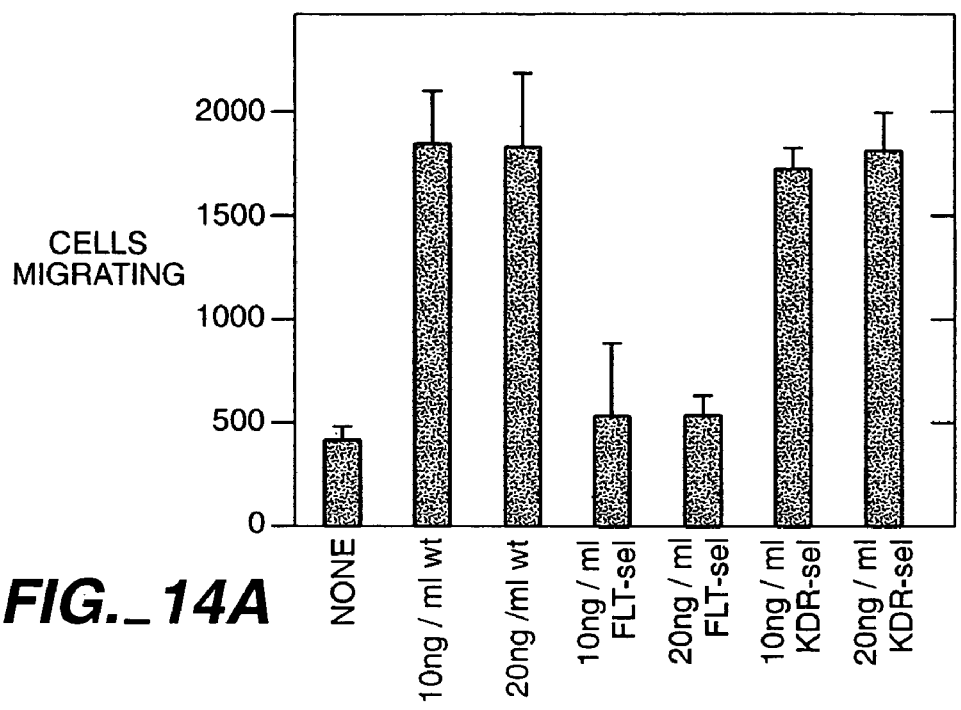
FIG._14A
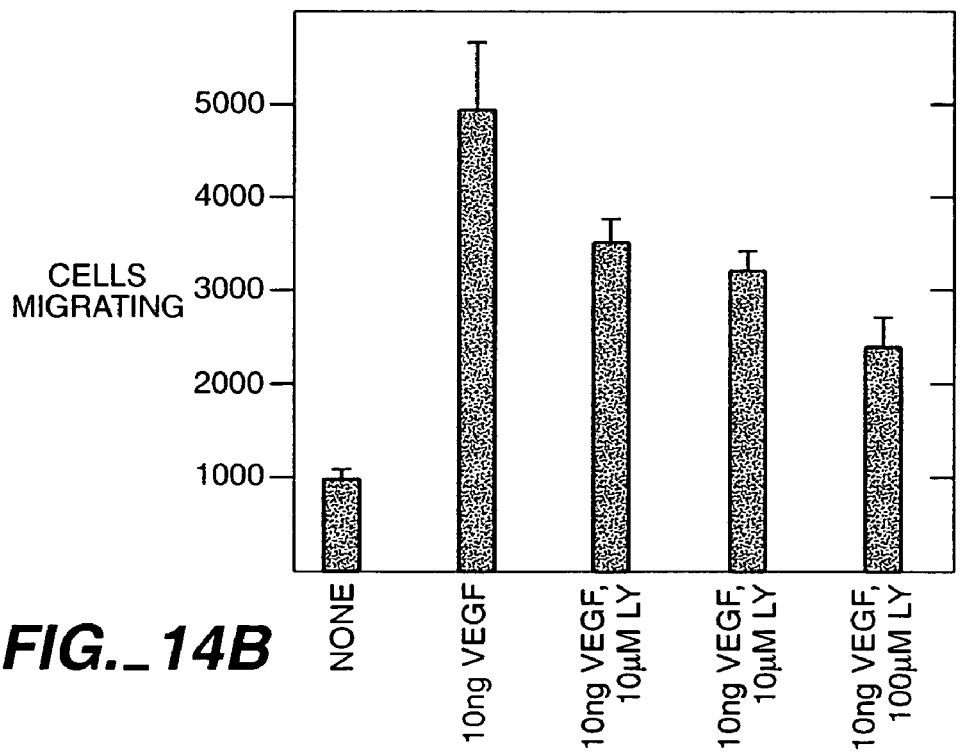
FIG._14B

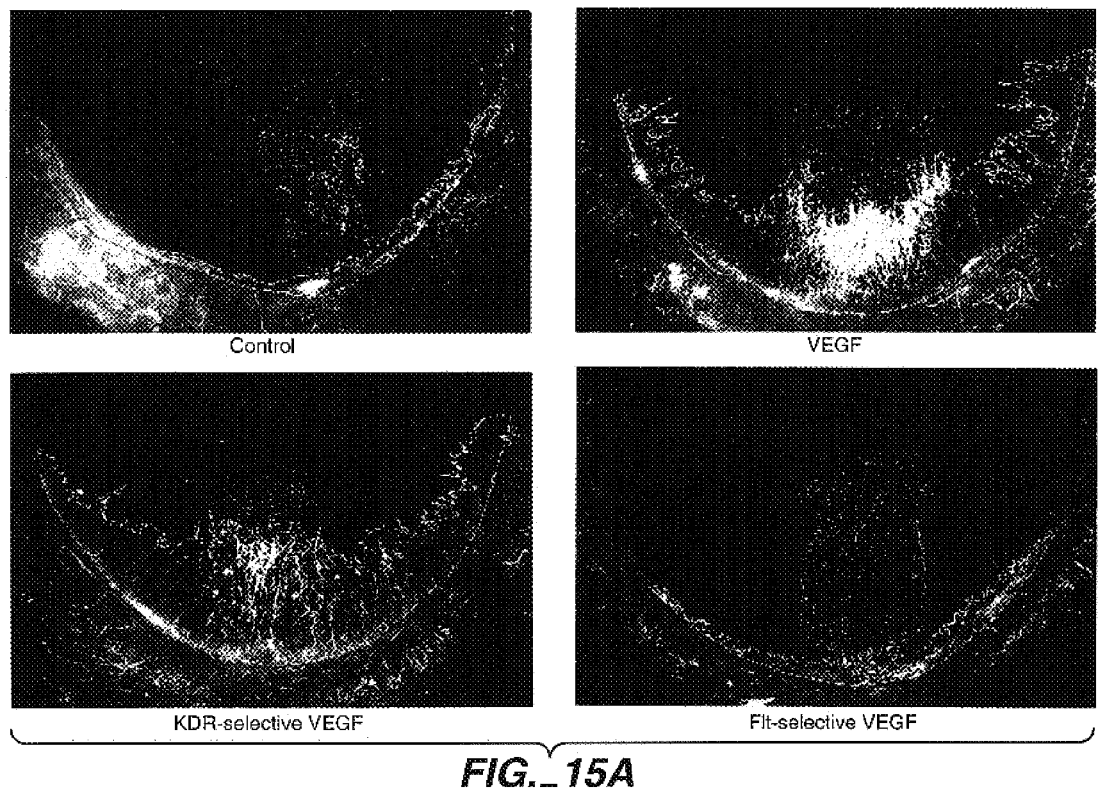
FIG._15A

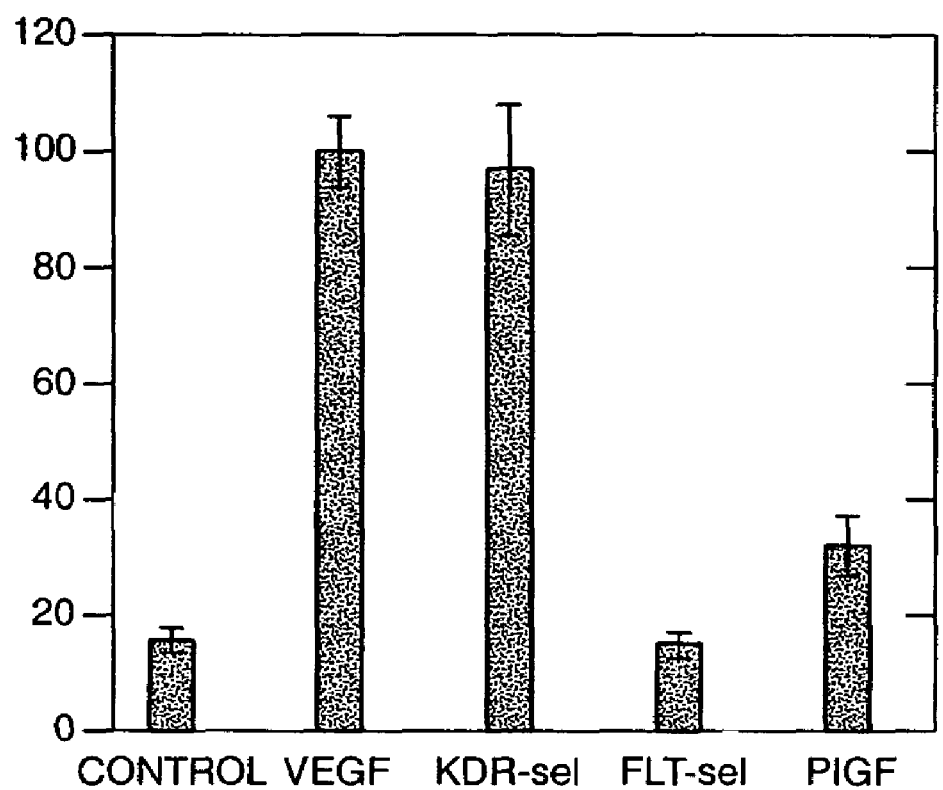
FIG._15B

VASCULAR ENDOTHELIAL CELL GROWTH FACTOR VARIANTS AND USES THEREOF

This application claims benefit of Provisional patent application Ser. No. 60/184,235 filed Feb. 23, 2000 and claims benefit of Provisional patent application Ser. No. 60/129,788 filed Apr. 16, 1999.

FIELD OF THE INVENTION

The present invention relates to vascular endothelial cell growth factor (VEGF) variants, to methods for preparing such variants, and to methods, compositions and assays utilizing such variants. In particular, the invention relates to VEGF variants which have binding affinity properties for the VEGF receptors, KDR and FLT-1, different from that of native VEGF.

BACKGROUND OF THE INVENTION

The two major cellular components of the vasculature are the endothelial and smooth muscle cells. The endothelial cells form the lining of the inner surface of all blood vessels and constitute a nonthrombogenic interface between blood and tissue. In addition, endothelial cells are an important component for the development of new capillaries and blood vessels. Thus, endothelial cells proliferate during the angiogenesis, or neovascularization, associated with tumor growth and metastasis, as well as a variety of non-neoplastic diseases or disorders.

Various naturally occurring polypeptides reportedly induce the proliferation of endothelial cells. Among those polypeptides are the basic and acidic fibroblast growth factors (FGF), Burgess and Maciag, *Annual Rev. Biochem.*, 58:575 (1989), platelet-derived endothelial cell growth factor (PD-ECGF), Ishikawa et al., *Nature,* 338:557 (1989), and vascular endothelial growth factor (VEGF), Leung et al., *Science,* 246:1306 (1989); Ferrara and Henzel, *Biochem. Biophys. Res. Commun.,* 161:851 (1989); Tischer et al., *Biochem. Biophys. Res. Commun.,* 165:1198 (1989); Ferrara et al., PCT Pat. Pub. No. WO 90/13649 (published Nov. 15, 1990).

VEGF was first identified in media conditioned by bovine pituitary follicular or folliculostellate cells. Biochemical analyses indicate that bovine VEGF is a dimeric protein with an apparent molecular mass of approximately 45,000 Daltons and with an apparent mitogenic specificity for vascular endothelial cells. DNA encoding bovine VEGF was isolated by screening a cDNA library prepared from such cells, using oligonucleotides based on the amino-terminal amino acid sequence of the protein as hybridization probes.

Human VEGF was obtained by first screening a cDNA library prepared from human cells, using bovine VEGF cDNA as a hybridization probe. One cDNA identified thereby encodes a 165-amino acid protein having greater than 95% homology to bovine VEGF; this 165-amino acid protein is typically referred to as human VEGF (hVEGF) or $VEGF_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. [See Leung et al., *Science,* 246:1306 (1989)].

Although a vascular endothelial cell growth factor could be isolated and purified from natural sources for subsequent therapeutic use, the relatively low concentrations of the protein in follicular cells and the high cost, both in terms of effort and expense, of recovering VEGF proved commercially unavailing. Accordingly, further efforts were undertaken to clone and express VEGF via recombinant DNA techniques. [See, e.g., *Laboratory Investigation,* 72:615 (1995), and the references cited therein].

VEGF has been reported to be useful for treating conditions in which a selected action on the vascular endothelial cells, in the absence of excessive tissue growth, is important, for example, diabetic ulcers and vascular injuries resulting from trauma such as subcutaneous wounds. VEGF, a vascular (artery and venus) endothelial cell growth factor, can restore cells that are damaged, a process referred to as vasculogenesis, and can stimulate the formulation of new vessels, a process referred to as angiogenesis. [See, e.g., Ferrara et al., *Endocrinol. Rev.,* 18:4–25 (1997)]. VEGF is expressed in a variety of tissues as multiple homodimeric forms (121, 165, 189, and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release (a) diffusible form(s) of VEGF. Amino acid sequencing of the carboxy terminal peptide identified after plasmin cleavage is $Arg_{110}$–$Ala_{111}$. Amino terminal "core" protein, VEGF (1–110) isolated as a homodimer, binds neutralizing monoclonal antibodies (such as the antibodies referred to as 4.6.1 and 3.2E3.1.1) and soluble forms of FLT-1 and KDR receptors with similar affinity compared to the intact $VEGF_{165}$ homodimer.

VEGF contains two sites that are responsible respectively for binding to the KDR (kinase domain region) and FLT-1 (FMS-like tyrosine kinase) receptors. These receptors are believed to exist only on endothelial (vascular) cells. VEGF production increases in cells that become oxygen-depleted as a result of, for example, trauma and the like, thereby allowing VEGF to bind to the respective receptors to trigger the signaling pathways that give rise to a biological response. For example, the binding of VEGF to such receptors may lead to increased vascular permeability, causing cells to divide and expand to form new vascular pathways— i.e., vasculogenesis and angiogenesis. [See, e.g., Malavaud et al., *Cardiovascular Research,* 36:276–281 (1997)]. It is reported that VEGF-induced signaling through the KDR receptor is responsible for the mitogenic effects of VEGF and possibly, to a large extent, the angiogenic activity of VEGF. [Waltenberger et al., *J. Biol. Chem.,* 269:26988–26995 (1994)]. The biological role(s) of FLT-1, however, is less well understood.

The sites or regions of the VEGF protein involved in receptor binding have been identified and found to be proximately located. [See, Weismann et al., *Cell,* 28:695–704 (1997); Muller et al., *Proc. Natl. Acad. Sci.,* 94:7192–7197 (1997); Muller et al., *Structure,* 5:1325–1338 (1997); Fuh et al., *J. Biol. Chem.,* 273:11197–11204 (1998)]. The KDR receptor has been found to bind VEGF predominantly through the sites on a loop which contains arginine (Arg or R) at position 82 of VEGF, lysine (Lys or K) at position 84, and histidine (His or H) at position 86. The FLT-1 receptor has been found to bind VEGF predominantly through the sites on a loop which contains aspartic acid (Asp or D) at position 63, glutamic acid (Glu or E) at position 64, and glutamic acid (Glu or E) at position 67. [Keyt et al., *J. Biol. Chem.,* 271:5638–5646 (1996)]. Based on the crystal structure of VEGF and functional mapping of the KDR binding site of VEGF, it has further been found that VEGF engages KDR receptors using two symmetrical binding sites located at opposite ends of the molecule. Each site is composed of two "hot spots" for binding that consist of residues from both subunits of the VEGF homodimer. [Muller et al., supra]. Two of these binding determinants are located within the dominant hot spot on a short, 3-stranded β-sheet that is conserved in transforming growth factor β2 (TGF-β) and platelet-derived growth factor (PDGF).

Certain VEGF-related molecules that selectively bind to one receptor over the other have been identified. A molecule, PlGF, shares 53% identity with the PDGF-like domain of VEGF. PlGF appears to bind Flt-1 with high affinity but is unable to react with KDR. As described in the literature, PlGF has displayed great variability in mitogenic activity for endothelial cells [Maglione et al., *Proc. Natl. Acad. Sci.*, 88:9267–9271 (1991); Park et al., *J. Biol. Chem.*, 269: 25646–25654 (1994); Sawano et al., *Cell Growth & Differentiation*, 7:213–221 (1996); Landgren et al., *Oncogene*, 16:359–367 (1998)].

Recently, Ogawa et al. described a gene encoding a polypeptide (called VEGF-E) with about 25% amino acid identity to mammalian VEGF. The VEGF-E was identified in the genome of Orf virus (NZ-7 strain), a parapoxvirus that affects sheep and goats and occasionally, humans, to generate lesions with angiogenesis. The investigators conducted a cell proliferation assay and reported that VEGF-E stimulated the growth of human umbilical vein endothelial cells as well as rat liver sinusoidal endothelial cells to almost the same degree as human VEGF. Binding studies were also reported. A competition experiment was conducted by incubating cells that overexpressed either the KDR receptor or the FLT-1 receptor with fixed amounts of $^{125}$I-labeled human VEGF or VEGF-E and then adding increasing amounts of unlabeled human VEGF or VEGF-E. The investigators reported that VEGF-E selectively bound KDR receptor as compared to FLT-1. [Ogawa et al., *J. Biological Chem.*, 273:31273–31281 (1998)].

Meyer et al., *EMBO J.*, 18:363–374 (1999), have also identified a member of the VEGF family which is referred to as VEGF-E. The VEGF-E molecule reported by Meyer et al. was identified in the genome of Orf virus strain D1701. In vitro, the VEGF-E was found to stimulate release of tissue factor and stimulate proliferation of vascular endothelial cells. In a rabbit in vivo model, the VEGF-E stimulated angiogenesis in the rabbit cornea. Analysis of the binding properties of the VEGF-E molecule reported by Meyer et al., in certain assays revealed the molecule selectively bound to the KDR receptor as compared to the FLT-1 receptor. See also, Wise et al., *Proc. Natl. Acad. Sci.*, 96:3071–3076 (1999).

Olofsson et al., *Proc. Natl. Acad. Sci.*, 95:11709–11714 (1998) report that a protein referred to as "VEGF-B" selectively binds FLT-1. The investigators disclose a mutagenesis experiment wherein the Asp63, Asp64, and Glu67 residues in VEGF-B were mutated to alanine residues. Analysis of the binding properties of the mutated form of VEGF-B revealed that the mutant protein exhibited a reduced affinity to FLT-1.

SUMMARY OF THE INVENTION

Applicants have identified VEGF variants which include at least one amino acid mutation (as compared to the native VEGF amino acid sequence), particularly at least one amino acid mutation at or between amino acid positions 17 to 25 and/or positions 63 to 65. Applicants have also identified VEGF variants which include at least one amino acid mutation (as compared to the native VEGF amino acid sequence) at positions 43, 46, 79 or 83, and particularly which include amino acid substitutions to alanine at each of positions 43, 46, 79 and 83. Applicants surprisingly found that various VEGF variants exhibited altered binding affinities with respect to the KDR and FLT-1 receptors (as compared to native VEGF) and further exhibited selective binding affinity for the KDR receptor or FLT-1 receptor.

The invention provides VEGF variants which include at least one amino acid mutation (as compared to the native VEGF amino acid sequence) and have selective binding affinity for the KDR receptor. Optionally, the at least one amino acid mutation comprises an amino acid substitution(s) in a native VEGF polypeptide.

In one embodiment, the invention provides VEGF variants comprising at least one amino acid mutation at or between positions 17 to 25 of VEGF. Optionally, such VEGF variants will comprise an amino acid substitution at or between positions 17 to 25. Particular amino acid substitutions include F17I, M18E, Y21L, Y21F, Q22R, Q22K, Q22E, Y25S or Y25I. In a preferred embodiment, such VEGF variants will include at least one amino acid substitution at positions 18 and/or 21 of VEGF, wherein the methionine amino acid residue at position 18 is substituted with glutamic acid and/or the tyrosine amino acid residue at position 21 is substituted with leucine.

In another embodiment, the invention provides VEGF variants comprising at least one amino acid mutation at or between positions 63 to 66 of VEGF. Optionally, such VEGF variants will comprise an amino acid substitution at or between positions 63 to 66. Particular amino acid substitutions include D63S, G65M, G65A, L66R or L66T. Preferred VEGF variants have one or more amino acid substitutions at positions 63, 65, and/or 66 of VEGF, wherein the amino acid residue aspartic acid at position 63 is substituted with serine, the amino acid residue glycine at position 65 is substituted with methionine, and/or the amino acid residue leucine at position 66 is substituted with arginine.

Further preferred VEGF variants will include multiple (i.e., more than one) amino acid mutations at positions 63, 65, and/or 66 of VEGF and/or one or more amino acid mutations at one or more of positions 17, 18, 21, 22, and/or 25 of VEGF. Even more preferably, the VEGF variants comprise one or more amino acid substitutions at positions 18 and/or 21 of VEGF, wherein position 18 is substituted with glutamic acid and/or position 21 is substituted with leucine, and one or more amino acid substitutions at positions 63, 65, and/or 66 of VEGF, wherein position 63 is substituted with serine, position 65 is substituted with methionine, and/or position 66 is substituted with arginine. Most preferably, the VEGF variants may include one of the following groups of amino acid substitutions: M18E, Y21L, Q22R, Y25S; D63S, G65M, L66R; M18E, D63S, G65M, L66R; or Y21L, D63S, G65M, L66R.

In a preferred embodiment, the VEGF variant is a polypeptide comprising the VEGF165 amino acid sequence which includes one or more amino acid substitutions described in the present application.

Additional preferred VEGF variants comprising multiple amino acid substitutions at such positions in the VEGF sequence are described in Table 2.

In a further embodiment, the invention provides VEGF variants which have selective binding affinity for the FLT-1 receptor, and preferably such VEGF variants will include one or more amino acid mutations at one or more of positions 43, 46, 79 or 83. Preferably, such FLT-1 selective VEGF variants will comprise multiple (i.e., more than one) amino acid mutations at positions 43, 46, 79 and/or 83 of VEGF. Even more preferably, the FLT-1 selective VEGF variants will comprise one or more amino acid substitutions to alanine at positions 43, 46, 79 and/or 83 of VEGF. Most preferably, the FLT-1 selective VEGF variants will comprise the set of amino acid substitutions: 143A, 146A, Q79A, and 183A.

In another aspect, the invention provides isolated nucleic acids encoding the VEGF variants described herein. Expression vectors capable of expressing the VEGF variants of the invention, host cells containing such vectors, and methods of producing VEGF variants by culturing the host cells under conditions to produce the VEGF variants are also provided.

In additional embodiments, the invention provides compositions comprising a VEGF variant and a carrier. Optionally, the carrier may be a pharmaceutically-acceptable carrier.

The invention further provides methods for treating conditions in which vasculogenesis or angiogenesis is desirable, such as trauma to the vascular network, for example, from surgical incisions, wounds, lacerations, penetration of blood vessels, and surface ulcers. In the methods, an effective amount of VEGF variant can be administered to a mammal having such condition(s).

The invention also provides diagnostic methods for using the VEGF variants in vitro. In one embodiment, the methods include assaying cells or tissue using VEGF variant(s) to detect the presence or absence of the KDR and/or FLT-1 receptor.

Finally, the invention provides kits and articles of manufacture containing the VEGF variant(s) disclosed herein.

BRIEF DESCRIPTION OF THE DRAWINGS

FIGS. 1A and 1B show the nucleotide sequence and putative amino acid sequence of the 165-amino acid native ("wild type") VEGF.

FIG. 2 shows the ELISA assay titration curve for the native-VEGF (8–109).

FIG. 3 shows the KIRA assay titration curve for the native VEGF (8–109).

FIG. 4 shows the HUVEC proliferation assay titration curve for the native VEGF (8–109).

FIG. 5 shows the binding affinities for KDR by native VEGF ("WT VEGF"), LK-VRB-2s* (KDR selective variant) and Flt-1-sel (Flt-1 selective variant) as measured by competitive displacement of $^{125}$I-VEGF (1–165) from KDR expressing NIH3T3 cells, using various concentrations of ligand. The assay is described in detail in Example 7. Each point represents the average of duplicate determinations, and errors are estimated to be less than 15% of the values.

FIG. 6 shows the binding affinities for Flt-1 by native VEGF ("WT VEGF"), LK-VRB-2s* (KDR selective variant) and Flt-1-sel (Flt-1 selective variant) as measured by competitive displacement of $^{125}$I-VEGF (1–165) from FLT-1 expressing NIH3T3 cells, using various concentrations of ligand. The assay is described in detail in Example 7. Each point represents the average of duplicate determinations, and errors are estimated to be less than 15% of the values.

FIG. 7 shows a table identifying fold reduction in binding of various VEGF alanine substitution variants. As described in Example 8, protein ELISAs were performed with the various alanine variants. Listed for each residue is the ratio of the $IC_{50}$ of the variant to the $IC_{50}$ of native VEGF (1–109), representing the fold reduction in binding of the variant compared to the native VEGF. $IC_{50}$s for the native VEGF (1–109) are shown in parentheses. Residues shown in bold face were used to generate the Flt-1 selective variant.

To generate KDR selective variants, the mutated regions were divided into five groups as shown, and the first four were used to construct libraries for subsequent phage display selections. Residues marked with an asterisk (*) were soft randomized for a 50% bias toward wild type, and residues marked with two asterisks were hard randomized.

FIG. 8A shows the results of a radio-immuno receptor binding assay (RIA) in which the Flt-1 selective variant ("Flt-1-sel") was shown to have at least 470-fold reduced KDR binding affinity. The binding affinity for native VEGF ("WT VEGF") is also shown. Each point represents the average of duplicate determinations, and errors are estimated to be less than 15% of the values.

FIG. 8B shows the results of a radio-immuno receptor binding assay (RIA) in which the Flt-1 selective variant ("Flt-1-sel") was shown to have binding affinity for FLT-1 similar to that exhibited by native VEGF ("WT VEGF"). Each point represents the average of duplicate determinations, and errors are estimated to be less than 15% of the values.

FIG. 9 shows the results of a KIRA assay measuring the ability of native VEGF ("WT VEGF") and Flt-1 selective variant ("Flt-1-sel") to induce KDR phosphorylation.

FIG. 10 shows the results of a HUVEC proliferation assay measuring the ability of native VEGF ("WT VEGF") and Flt-1 selective variant ("Flt-1-sel") to induce HUVEC cell proliferation. Each data point was the average of triplicate experiments with an estimated error of 10–20%.

FIG. 11 shows the results of a gelatin zymography analysis to determine the ability of native VEGF, LK-VRB-2s* (KDR selective variant), Flt- sel (Flt-1 selective variant), and PlGF to stimulate MMP-9 secretion by human ASMC cells. The zymogram shown is one of two independent experiments. Fold change represents the relative band density.

FIGS. 12A and 12B illustrate Western blot analyses conducted to determine activation of MAP kinases by native VEGF ("WT VEGF"), Flt-sel (Flt-1 selective variant), and KDR selective variant ("KDR-sel"). The assay is described in detail in Example 10.

FIGS. 13A and 13B illustrates Western blot analyses conducted to determine the role of native VEGF ("wt" or "VEGF"), KDR-selective variant ("KDR-sel"), and Flt-1 selective variant ("Flt-sel") and KDR in PLC-gamma and PI3'-kinase phosphorylation. The assays are described in detail in Example 11.

FIGS. 14A and 14B show bar diagrams illustrating the results of HUVEC migration assays conducted in modified Boyden chambers. FIG. 14A shows the HUVEC migration achieved by the indicated concentrations of native VEGF ("wt"), Flt-selective variant ("Flt-sel"), and KDR selective variant ("KDR-sel"). FIG. 14B shows the results of an experiment in which addition of PI3'-kinase inhibitor ("LY") impaired HUVEC migration in response to native VEGF ("VEGF"). Experiments were performed in triplicate, and error bars represent the standard error.

FIGS. 15A and 15B show the results of an in vivo corneal pocket angiogenesis assay. The slides in FIG. 15A show representative examples of the extent of corneal angiogenesis in response to control treatment, native VEGF ("VEGF"), KDR-selective variant and Flt-selective variant. FIG. 15B illustrates a quantitative analysis of the surface areas of corneal angiogenesis resulting from control treatment, native VEGF ("VEGF"), KDR-selective variant ("KDR-sel"), Flt-1 selective

DETAILED DESCRIPTION OF THE INVENTION

A. Definitions

The terms "VEGF" and "native VEGF" as used herein refer to the 165-amino acid vascular endothelial cell growth factor and related 121-, 189-, and 206- amino acid vascular endothelial cell growth factors, as described by Leung et al., *Science*, 246:1306 (1989) and Houck et al., *Mol. Endocrin.*, 5:1806 (1991), (and further provided in FIGS. 1A and 1B), together with the naturally occurring allelic and processed forms thereof. The terms "VEGF" and "native VEGF" are also used to refer to truncated forms of the polypeptide comprising amino acids 8 to 109 or 1 to 109 of the 165-amino acid vascular endothelial cell growth factor. Reference to any such forms of VEGF may be identified in the present application, e.g., by "VEGF (8–109)," "VEGF (1–109)" or "VEGF165 or VEGF (1–165)." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF preferably has binding affinity for the KDR and FLT-1 receptors comparable to native VEGF.

The term "VEGF variant" as used herein refers to a VEGF polypeptide which includes one or more amino acid mutations in the native VEGF sequence and has selective binding affinity for either the KDR receptor or the FLT-1 receptor. In one embodiment, the VEGF variant having selective binding affinity for the KDR receptor includes one or more amino acid mutations in any one of positions 17 to 25 and/or 63 to 66 of the native VEGF sequence. Optionally, the one or more amino acid mutations include amino acid substitution(s). Preferred KDR selective VEGF variants include one or more amino acid mutations and exhibit binding affinity to the KDR receptor which is equal to or greater ($\geq$) than the binding affinity of native VEGF to the KDR receptor, and even more preferably, the VEGF variants exhibit less binding affinity (<) to the FLT-1 receptor than the binding affinity exhibited by native VEGF to FLT-1. When binding affinity of such VEGF variant to the KDR receptor is approximately equal (unchanged) or greater than (increased) as compared to native VEGF, and the binding affinity of the VEGF variant to the FLT-1 receptor is less than or nearly eliminated as compared to native VEGF, the binding affinity of the VEGF variant, for purposes herein, is considered "selective" for the KDR receptor. Preferred KDR selective VEGF variants of the invention will have at least 10-fold less binding affinity to FLT-1 receptor (as compared to native VEGF), and even more preferably, will have at least 100-fold less binding affinity to FLT-1 receptor (as compared to native VEGF). The respective binding affinity of the VEGF variant may be determined by ELISA, RIA, and/or BIAcore assays, known in the art and described further in the Examples below. Preferred KDR selective VEGF variants of the invention will also exhibit activity in KIRA assays (such as described in the Examples) reflective of the capability to induce phosphorylation of the KDR receptor. Preferred KDR selective VEGF variants of the invention will additionally or alternatively induce endothelial cell proliferation (which can be determined by known art methods such as the HUVEC proliferation assay in the Examples). Induction of endothelial cell proliferation is presently believed to be the result of signal transmission by the KDR receptor.

In one embodiment, the VEGF variant having selective binding affinity for the FLT-1 receptor includes one or more amino acid mutations in any one of positions 43, 46, 79 or 83 of the native VEGF sequence. Optionally, the one or more amino acid mutations include amino acid substitution(s), and preferably, amino acid substitutions to alanine. Preferred FLT-1 selective VEGF variants include one or more amino acid mutations and exhibit binding affinity to the FLT-1 receptor which is equal to or greater ($\geq$) than the binding affinity of native VEGF to the FLT-1 receptor, and even more preferably, such VEGF variants exhibit less binding affinity (<) to the KDR receptor than the binding affinity exhibited by native VEGF to KDR. When binding affinity of such VEGF variant to the FLT-1 receptor is approximately equal (unchanged) or greater than (increased) as compared to native VEGF, and the binding affinity of the VEGF variant to the KDR receptor is less than or nearly eliminated as compared to native VEGF, the binding affinity of the VEGF variant, for purposes herein, is considered "selective" for the FLT-1 receptor. Preferred FLT-1 selective VEGF variants of the invention will have at least 10-fold less binding affinity to KDR receptor (as compared to native VEGF), and even more preferably, will have at least 100-fold less binding affinity to KDR receptor (as compared to native VEGF). The respective binding affinity of the VEGF variant may be determined by ELISA, RIA, and/or BIAcore assays, known in the art and described further in the Examples below.

For purposes of shorthand designation of VEGF variants described herein, it is noted that numbers, refer to the amino acid residue position along the amino acid sequence of the putative native VEGF (provided in Leung et al., supra and Houck et al., supra.). Amino acid identification uses the single-letter alphabet of amino acids, i.e.,

| Asp | D | Aspartic acid | Ile | I | Isoleucine |
| --- | --- | --- | --- | --- | --- |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Praline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences-being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refer to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content because deliberate or inadvertent mutations may occur. Mutant progeny that have the same functionality as screened for in the originally transformed cell are included. Where distinct designations are intended, it will be clear from the context.

"Plasmids" are designated by a lower case "p" preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

The term "VEGF receptor" as used herein refers to a cellular receptor for VEGF, ordinarily a cell-surface receptor found on vascular endothelial cells, as well as fragments and variants thereof which retain the ability to bind VEGF (such as fragments or truncated forms of the receptor extracellular domain). One example of a VEGF receptor is the fms-like tyrosine kinase (FLT or FLT-1), a transmembrane receptor in the tyrosine kinase family. The term "FLT-1 receptor" used in the application refers to the VEGF receptor described, for instance, by DeVries et al., *Science,* 255:989 (1992); and Shibuya et al., *Oncogene,* 5:519 (1990). The full length FLT-1 receptor comprises an extracellular domain, a transmembrane domain, and an intracellular domain with tyrosine kinase activity. The extracellular domain is involved in the binding of VEGF, whereas the intracellular domain is involved in signal transduction. Another example of a VEGF receptor is the KDR receptor (also referred to as FLK-1). The term "KDR receptor"used in the application refers to the VEGF receptor described, for instance, by Matthews et al., *Proc. Nat. Acad. Sci.,* 88:9026 (1991); and Terman et al., *Oncogene,* 6:1677 (1991); Terman et al., *Biochem. Biophys. Res. Commun.,* 187:1579 (1992).

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. Intermittent administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cows, horses, sheep, or pigs. Preferably, the mammal is human.

Administration "in combination with" one or more further therapeutic agents includes simultaneous (concurrent) and consecutive administration in any order.

B. Methods and Compositions

1. Preparation of VEGF Variants

Amino acid sequence variants of VEGF can be prepared by mutations in the VEGF DNA. Such variants include, for example, deletions from, insertions into or substitutions of residues within the amino acid sequence shown in Leung et al., supra and Houck et al., supra. Any combination of deletion, insertion, and substitution may be made to arrive at the final construct having the desired activity. Obviously, the mutations that will be made in the DNA encoding the variant must not place the sequence out of reading frame and preferably will not create complementary regions that could produce secondary mRNA structure [see EP 75,444A].

The VEGF variants optionally are prepared by site-directed mutagenesis of nucleotides in the DNA encoding the native VEGF or phage display techniques, thereby producing DNA encoding the variant, and thereafter expressing the DNA in recombinant at cell culture.

While the site for introducing an amino acid sequence variation is predetermined, the mutation per se need not be predetermined. For example, to optimize the performance of a mutation at a given site, random mutagenesis may be conducted at the target codon or region and the expressed VEGF variants screened for the optimal combination of desired activity. Techniques for making substitution mutations at predetermined sites in DNA having a known sequence are well-known, such as, for example, site-specific mutagenesis.

Preparation of the VEGF variants described herein is preferably achieved by phage display techniques, such as those described in Example 1.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length as well as intrasequence insertions of single or multiple amino acid residues. Intrasequence insertions (i.e., insertions within the native VEGF sequence) may range generally from about 1 to 10 residues, more preferably 1 to 5. An example of a terminal insertion includes a fusion of a signal sequence, whether heterologous or homologous to the host cell, to the N-terminus to facilitate the secretion from recombinant hosts.

Additional VEGF variants are those in which at least one amino acid residue in the native VEGF has been removed and a different residue inserted in its place. Such substitutions may be made in accordance with those shown in Table 1.

TABLE 1

| Original Residue | Exemplary Substitutions |
|---|---|
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu:; tyr |
| Ser (S) | thr |
| Thr (T) | ser |
| Trp (W) | tyr |
| Tyr (Y) | trp; phe |
| Val (V) | ile; leu |

Changes in function or immunological identity may be made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in the VEGF variant properties will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (e) a residue having an electronegative side chain is substituted for (or by) a residue having an electropositive charge; or (f) a residue having a bulky side chain, e.g., phenylalanine, is substituted for (or by) one not having such a side chain, e.g., glycine.

The effect of the substitution, deletion, or insertion may be evaluated readily by one skilled in the art using routine screening assays. For example, a phage display-selected VEGF variant may be expressed in recombinant cell culture, and, optionally, purified from the cell culture. The VEGF variant may then be evaluated for KDR or FLT-1 receptor binding affinity and other biological activities, such as those disclosed in the present application. The binding properties or activities of the cell lysate or purified VEGF variant can be screened in a suitable, screening assay for a desirable characteristic. For example, a change in the immunological character of the VEGF variant as compared to native VEGF, such as affinity for a given antibody, may be desirable. Such a change may be measured by a competitive-type immunoassay, which can be conducted in accordance with techniques known in the art. The respective receptor binding affinity of the VEGF variant may be determined by ELISA, RIA, and/or BIAcore assays, known in the art and described further in the Examples below. Preferred VEGF variants of the invention will also exhibit activity in KIRA assays (such as described in the Examples) reflective of the capability to induce phosphorylation of the KDR receptor. Preferred VEGF variants of the invention will additionally or alternatively induce endothelial cell proliferation (which can be determined by known art methods such as the HUVEC proliferation assay in the Examples).

VEGF variants may be prepared by techniques known in the art, for example, recombinant methods. Isolated DNA used in these methods is understood herein to mean chemically synthesized DNA, cDNA, chromosomal, or extrachromosomal DNA with or without the 3'- and/or 5'-flanking regions. Preferably, the VEGF variants herein are made by synthesis in recombinant cell culture.

For such synthesis, it is first necessary to secure nucleic acid that encodes a VEGF or VEGF variant. DNA encoding a VEGF molecule may be obtained from bovine pituitary follicular cells by (a) preparing a cDNA library from these cells, (b) conducting hybridization analysis with labeled DNA encoding the VEGF or fragments thereof (up to or more than 100 base pairs in length) to detect clones in the library containing homologous sequences, and (c) analyzing the clones by restriction enzyme analysis and nucleic acid sequencing to identify full-length clones. If full-length clones are not present in a cDNA library, then appropriate fragments may be recovered from the various clones using the nucleic acid sequence information disclosed herein for the first time and ligated at restriction sites common to the clones to assemble a full-length clone encoding the VEGF. Alternatively, genomic libraries will provide the desired DNA.

Once this DNA has been identified and isolated from the library, it is ligated into a replicable vector for further cloning or for expression.

In one example of a recombinant expression system, a VEGF-encoding gene is expressed in a cell system by transformation with an expression vector comprising DNA encoding the VEGF. It is preferable to transform host cells capable of accomplishing such processing so as to obtain the VEGF in the culture medium or periplasm of the host cell, i.e., obtain a secreted molecule.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

"Transformation" refers to introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, *Proc. Natl. Acad. Sci*. (*USA*), 69: 2110 (1972) and Mandel et al., *J. Mol. Biol.,* 53: 154 (1970), is generally used for prokaryotes or other cells that contain substantial cell-wall barriers. For mammalian cells without such cell walls, the calcium phosphate precipitation method of Graham and van der Eb, *Virology,* 52: 456–457 (1978), is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.,* 130: 946 (1977) and Hsiao et al., *Proc. Natl. Acad. Sci*. (*USA*), 76: 3829 (1979). However, other methods for introducing DNA into cells such as by nuclear injection or by protoplast fusion may also be used.

The vectors and methods disclosed herein are suitable for use in host cells over a wide range of prokaryotic and eukaryotic organisms.

In general, of course, prokaryotes are preferred for the initial cloning of DNA sequence and construction of the vectors useful in the invention. For example, *E. coli* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

Prokaryotes may also be used for expression. The aforementioned strains, as well as *E. coli* strains W3110 (F-, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site as well as marking sequences that are capable of providing phenotypic selection in transformed cells. For example, *E. coli* is typically transformed using pBR322, a plasmid derived from an *E. coli* species (see, e.g., Bolivar et al., *Gene,* 2:95 (1977)]. pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems [Chang et al., *Nature,* 375:615 (1978); Itakura et al., *Science,* 198:1056 (1977); Goeddel et al., *Nature,* 281:544 (1979)] and a tryptophan (trp) promoter system [Goeddel et al., *Nucleic Acids Res.,* 8:4057 (1980); EPO Appl. Publ. No. 0036,776]. While these are the most commonly used, other microbial promoters have been discovered and utilized, and details concerning their nucleotide sequences have been published, enabling a skilled worker to ligate them functionally with plasmid vectors [see, e.g., Siebenlist et al., *Cell,* 20:269 (1980)].

In addition to prokaryotes, eukaryotic microbes, such as yeast cultures, may also be used. *Saccharomyces cerevisiae,* or common baker's yeast, is the most commonly used among eukaryotic microorganisms, although a number of other strains are commonly available. For expression in *Saccharomyces*, the plasmid YRp7, for [Stinchcomb et al., *Nature,* 282:39 (1979); Kingsman et al., *Gene,* 7:141 (1979); Tschemper et al., *Gene,* 10:157 (1980)], is commonly used. This plasmid already contains the trp1 gene that provides a selection marker for a mutant strain of yeast lacking the ability to grow in tryptophan, for example, ATCC No. 44,076 or PEP4-1 [Jones, *Genetics,* 85:12 (1977)]. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland et al., *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [Tissue Culture, Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication [Fiers et al., *Nature,* 273:113 (1978)]. Smaller or larger SV40 fragments may also be used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both VEGF and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci. (USA)*, 77:4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using, by way of example, 6 percent polyacrylamide gel described by Goeddel et al., *Nucleic Acids Res.*, 8:4057 (1980).

To confirm correct sequences were constructed in plasmids, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9:309 (1981) or by the method of Maxam et al., *Methods of Enzymology*, 65:499 (1980).

After introduction of the DNA into the mammalian cell host and selection in medium for stable transfectants, amplification of DHFR-protein-coding sequences is effected by growing host cell cultures in the presence of approximately 20,000–500,000 nM concentrations of methotrexate (MTX), a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

2. Covalent Modifications of VEGF Variants

The VEGF variants of the invention may also comprise further modifications. Examples include covalent modification(s) to one or more amino acid residues. For example, cysteinyl residues may be reacted with haloacetates (and corresponding amines), such as chloroacetic acid or chloroacetamide, to give carboxymethyl or carboxyamidomethyl derivatives. Cysteinyl residues also may be derivatized by reaction with bromotrifluoroacetone; β-bromo-(5-imidozoyl)propionic acid; chloroacetyl phosphate; N-alkylmaleimides; 3-nitro-2-pyridyl disulfide; methyl 2-pyridyl disulfide; p-chloromercuribenzoate; 2-chloromercuri-4-nitrophenol; or chloro-7-nitrobenzo-2-oxa-1,3-diazole.

Another example includes derivatizing histidyl residues by reaction with diethylpyrocarbonate at pH 5.5–7.0. Parabromophenacyl bromide, a reaction that is preferably performed in 0.1M sodium cacodylate at pH 6.0, may be useful.

Lysinyl and amino terminal residues may be reacted with succinic or other carboxylic acid anhydrides. Derivatization with these agents has the effect of reversing the charge of the lysinyl residues. Other suitable reagents for derivatizing β-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. These reagents may also be used to modify the epsilon-amino group of lysine. Derivatization of arginine residues should be performed in alkaline conditions because the guanidine functional group has a high $pk_a$.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues may be iodinated using $^{125}I$ or $^{131}I$ by, for example, using the chloramine T method described infra, thereby preparing labeled proteins for use in radioimmunoassay.

Carboxyl side groups (aspartyl or glutamyl) may be selectively modified by reaction with carbodiimides (R'-N-C-N-R') such as 1-cyclohexyl-3-(2-morpholinyl-(4-ethyl)) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Derivatization with bifunctional agents is useful for crosslinking the VEGF variant to a water-insoluble support matrix or surface. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330;440 may be employed for protein immobilization.

Glutaminyl and asparaginyl residues are frequently deamidated to the corresponding glutamyl and aspartyl residues. Alternatively, these residues may be deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains [Creighton, *Proteins: Structure and Molecular Properties* 79–86 (W.H. Freeman & Co., San Francisco (1983))], acetylation of the N-terminal amine, and, in some instances, amidation of the C-terminal carboxyl group.

Further modifications include linking or fusing the VEGF or VEGF variant (or VEGF agonist) to a nonproteinaceous polymer such as polyethylene glycol. Such methods of pegylating proteins are known in the art.

The VEGF variant amino acid sequence may contain at least one amino acid sequence that has potential to be glycosylated through an N-linkage and that is not normally glycosylated in the native VEGF.

Introduction of an N-linked glycosylation site in the variant requires a tripeptidyl sequence of the formula: asparagine-X-serine or asparagine-X-threonine, wherein asparagine is the acceptor and X is any of the twenty genetically encoded amino acids except proline, which prevents glycosylation. [See Struck and Lennarz, in *The Biochemistry of Glycoproteins and Proteoglycans* 35 (Lennarz, ed., Plenum Press (1980)), Marshall, *Biochem. Soc. Symp.,* 40:17 (1974); and Winzler, in *Hormonal Proteins and Peptides* 1–15(Li, ed., Academic Press, New York (1973))]. The amino acid sequence variant herein is modified by substituting for the amino acid(s) at the appropriate site(s) the appropriate amino acids to effect glycosylation.

If O-linked glycosylation is to be employed, O-glycosidic linkage occurs in animal cells between N-acetylgalactosamine, galactose, or xylose and one of several hydroxyamino acids, most commonly serine or threonine, but also in some cases a 5-hydroxyproline or 5-hydroxylysine residue placed in the appropriate region of the molecule.

Glycosylation patterns for proteins produced by mammals are described in detail in *The Plasma Proteins: Structure, Function and Genetic Control* 271–315 (Putnam, ed., 2nd edition, Academic Press, New York. (1984)). In this chapter, asparagine-linked oligosaccharides are discussed, including their subdivision into at least three groups referred to as complex, high mannose, and hybrid structures, as well as O-glucosidically linked oligosaccharides.

Chemical and/or enzymatic coupling of glycosides to proteins can be accomplished using a variety of activated groups, for example, as described by Aplin and Wriston in *CRC Crit. Rev. Biochem.* 259–306 (1981). The advantages of the chemical coupling techniques are that they are relatively simple and do not need the complicated enzymatic machinery required for natural O- and N-linked glycosylation. Depending on the coupling mode used, the sugar(s) may be attached to (a) arginine or histidine, (b) free carboxyl groups such as those of glutamic acid or aspartic acid, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described more fully in PCT WO 87/05330 published Sep. 11, 1987.

Glycosylation patterns for proteins produced by yeast are described in detail by Tanner and Lehle, *Biochim. Biophys. Acta,* 906(1):81–99 (1987) and by Kukuruzinska et al., *Annu. Rev. Biochem.,* 56:915–944 (1987).

While glycosylation of native VEGF is not essential for bioactivity [Walter et al., *Laboratory Investigation,* 74:546 (1996)], the aforementioned methods may be employed to alter glycosylation of a VEGF variant, if desired.

3. Therapeutic and Diagnostic Methods

The invention also provides methods of using the disclosed VEGF variants. The methods include therapeutic methods, such as methods of inducing vasculogenesis or angiogenesis. The methods can also be directed to the treatment of traumata to the vascular network, in view of the proliferation of vascular endothelial cells that would surround the traumata. Examples of such traumata that could be so treated include, but are not limited to, surgical incisions, particularly those involving the heart, wounds, including lacerations, incisions, and penetrations of blood vessels, and surface ulcers involving the vascular endothelium such as diabetic, hemophiliac, and varicose ulcers. It is contemplated that preferred VEGF variants having selective binding affinity to the KDR receptor may be employed wherein it is desired to achieve KDR receptor activation but avoid potential side effects that may accompany FLT-1 receptor activation. Likewise, a preferred VEGF variant having selective binding affinity to the Flt-1 receptor may be employed wherein it is desired to achieve Flt-1 receptor activation but avoid potential side effects that may accompany KDR receptor activation.

The VEGF variant may be formulated and dosed in a fashion consistent with good medical practice taking into account the specific condition to be treated, the condition of the individual patient, the site of delivery of the VEGF variant, the method of administration, and other factors known to practitioners. "An effective amount" of a VEGF variant includes amounts that prevent; lessen the worsening of, alleviate, or cure the condition being treated or symptoms thereof.

VEGF variants may be prepared for storage or administration by mixing the VEGF variant having the desired degree of purity with physiologically acceptable carriers, excipients, or stabilizers. Suitable carrier vehicles and their formulation, inclusive of other human proteins, for example, human serum albumin, are described, for example, in *Remington's Pharmaceutical Sciences,* 16th ed., 1980, Mack Publishing Co., edited by Oslo et al. Typically, an appropriate amount of a pharmaceutically-acceptable salt is used in the formulation to render the formulation isotonic. Examples of the carrier include buffers such as saline, Ringer's solution, and dextrose solution. The pH of the solution is preferably from about 5.0 to about 8.0. For example, if the VEGF variant is water soluble, it may be formulated in a buffer such as phosphate or other organic acid salt at a pH of about 7.0 to 8.0. If a VEGF variant is only partially soluble in water, it may be prepared as a microemulsion by formulating it with a nonionic surfactant such as Tween, Pluronics, or PEG, e.g., Tween 80, in an amount of 0.04–0.05% (w/v), to increase its solubility.

Further carriers include sustained release preparations which include the formation of microcapsular particles and implantable articles. Examples of sustained release preparations include, for example, semipermeable matrices of solid hydrophobic polymers, which matrices are in the form of shaped articles, e.g., films, liposomes or microparticles. For preparing sustained-release VEGF variant compositions, the VEGF variant is preferably incorporated into a biodegradable matrix or microcapsule. A suitable material for this purpose is a polylactide, although other polymers of poly-(β-hydroxycarboxylic acids), such as poly-D-(-)-3-hydroxybutyric acid [EP 133,988A], can be used. Other biodegradable polymers such as, for example, poly(lactones), poly (acetals), poly(orthoesters), or poly(orthocarbonates) are also suitable.

For examples of sustained release compositions, see U.S. Pat. No. 3,773,919, EP 58,481A, U.S. Pat. No. 3,887,699, EP 158,277A, Canadian Patent No. 1176565, Sidman et al., *Biopolymers,* 22:547 (1983), and Langer et al., *Chem. Tech.,* 12:98 (1982).

It will be apparent to those persons skilled in the art that certain carriers may be more preferable depending upon, for instance, the route of administration and concentration of the VEGF variant being administered.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates, including cellulose or its derivatives, glucose, mannose, or dextrins; chelating agents such as EDTA; and sugar alcohols such as mannitol or sorbitol. The use of excipients, carriers, stabilizers, or other additives may result in the formation of salts of the VEGF variant.

When selecting carriers, excipients, stabilizers, or other additives, the selected compound(s) and corresponding degradation products should be nontoxic and avoid aggravating the condition treated and/or symptoms thereof. This can be determined by routine screening in animal models of the target disorder or, if such models are unavailable, in normal animals.

The VEGF variant to be used for therapeutic administration should be sterile. Sterility is readily accomplished by filtration through sterile filtration membranes (e.g., 0.2 micron membranes). The VEGF variant ordinarily will be stored in lyophilized form or as an aqueous solution. The pH of the VEGF variant compositions typically will be from about 5.0 to 8.0, although higher or lower pH values may also be appropriate in some instances.

Administration to a mammal may be accomplished by injection (e.g., intravenous, intraperitoneal, subcutaneous, intramuscular) or by other methods such as inhalation or infusion that ensure delivery to the bloodstream in an effective form. If the VEGF variant is to be used parenterally, therapeutic compositions containing the VEGF variant generally are placed into a container having a sterile access port, for example, an intravenous solution bag or vial having a stopper pierceable by a hypodermic injection needle.

Generally, where the condition permits, one may formulate and dose the VEGF variant for site-specific delivery. This is convenient in the case of wounds and ulcers.

When applied topically, the VEGF variant is suitably combined with additives, such as carriers, adjuvants, stabilizers, or excipients. As described above, when selecting additives for admixture with a VEGF variant, additives should be pharmaceutically acceptable and efficacious for their intended administration. Further, additives should not affect the activity of the VEGF variants. Examples of suitable topical formulations include ointment's, creams, gels, or suspensions, with or without purified collagen. The compositions also may be impregnated into transdermal patches, plasters, and bandages, preferably in liquid or semi-liquid form.

A gel formulation having the desired viscosity may be prepared by mixing a VEGF variant with a water-soluble polysaccharide, such as a cellulose derivative, or synthetic polymer, such as polyethylene glycol. The term "water soluble" as applied to the polysaccharides and polyethylene glycols is meant to include colloidal solutions and dispersions. In general, the solubility of, for example, cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, Li, Na, K, or Cs salts.

Examples of suitable polysaccharides include, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the VEGF variant held within it.

Preferably the polysaccharide is an etherified cellulose derivative, more preferably one that is well defined, purified, and listed in USP, for example, methylcellulose and the hydroxyalkyl cellulose derivatives, such as hydroxypropyl cellulose, hydroxyethyl cellulose, and hydroxypropyl methylcellulose. Most preferred herein is methylcellulose. For example, a gel formulation comprising methylcellulose preferably comprises about 2–5% methylcellulose and 300–1000 mg of VEGF variant per milliliter of gel. More preferably, the gel formulation comprises about 3% methylcellulose.

The polyethylene glycol useful for a gel formulation is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The dosage to be employed is dependent upon the factors described above. As a general proposition, the VEGF variant is formulated and delivered to the target site or tissue at a dosage capable of establishing in the tissue a VEGF variant level greater than about 0.1 ng/cc up to a maximum dose that is efficacious but not unduly toxic. This intra-tissue concentration should be maintained if possible by continuous infusion, sustained release, topical application, or injection at empirically determined frequencies.

It is within the scope hereof to combine the VEGF variant therapy with other novel or conventional therapies (e.g., known in the art growth factors such as aFGF, bFGF, HGF, PDGF, IGF, NGF, anabolic steroids, EGF or TGF-β) for enhancing the activity of any of the growth factors, including native VEGF, in promoting cell proliferation and repair. It is not necessary that such cotreatment drugs be included per se in the compositions of this invention, although this will be convenient where such drugs are proteinaceous. Such admixtures are suitably administered in the same manner and for, e.g., the same purposes as the VEGF variant used alone.

Effective dosages and schedules for administration may be determined empirically, and making such determinations is within the skill in the art.

The VEGF variants of the invention also have utility in diagnostic methods and assays. For instance, the VEGF variants may be employed in diagnostic assays to detect expression or presence of KRD receptor in cells and tissues. Various diagnostic assay techniques known in the art may be used, such as in vivo imaging assays, in vitro competitive binding assays, direct or indirect sandwich assays and immunoprecipitation assays conducted in either heterogeneous or homogeneous phases. The VEGF variants used in such assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S or $^{125}$I, a fluorescent or chemiluminescent compound, such as a fluorescein isothiocyanate, rhodamine, or luciferin, or an enzyme, such as alkaline phosphatase, beta-galactosidase, or horseradish peroxidase. Any method known in the art for conjugating the VEGF variant to the detectable moiety may be employed.

The VEGF variants may also be used for affinity purification of KDR receptor or Flt-1 receptor from a recombinant cell culture or natural sources. The VEGF variants can be immobilized on a suitable support, such as a resin or filter paper, using methods known in the art. The immobilized VEGF variant can then be contacted with the sample containing KDR receptor or Flt-1 receptor, and thereafter the support is washed with a suitable solvent that will remove substantially all the material in the sample except KDR receptor or Flt-1 receptor, which is bound to the VEGF variant. If desired, the support can be washed with another suitable solvent that will release the KDR receptor or Flt-1 receptor from the VEGF variant.

4. Articles of Manufacture

Articles of manufacture and kits are further provided by the present application. An article of manufacture such as a kit containing a VEGF variant useful for diagnostic assays or the treatment of conditions described herein comprises at least a container and a label. Suitable containers include, for example, bottles, vials, syringes, and test tubes. The containers may be formed from a variety of materials such as glass or plastic. The container holds a compositions that is useful for diagnosing or treating the condition and may have a sterile access port (for example, the container may be an intravenous solution bag or a vial having a stopper pierceable by a hypodermic injection needle). The active agent in the composition is the VEGF variant. The label on, or associated with, the container indicates that the composition is used for diagnostic purposes or treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use. The article of manufacture may also comprise a second or third container with another active agent as described above.

The following examples are offered for illustrative purposes only and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Selection of KDR-Specific VEGF Variants

To generate KDR-specific variants, two phage libraries were constructed in which residues of VEGF(1–109) found to be important for Flt-1 binding but not KDR binding were randomly mutated.

Phagemid Construction

To construct the phage libraries, a phagemid vector having cDNA encoding residues 1–109 of VEGF was first produced. Phagemid vector pB2105 (Genentech, Inc.) was produced by PCR amplification of the cDNA encoding residues 1–109 of VEGF, using primers that allowed subsequent ligation of Nsi I/Xba I restriction fragment into the phagemid vector, phGHam-g3 (Genentech, Inc.). This introduced an amber codon immediately following residue 109 and fused the VEGF 1–109 cDNA to the C-terminal half of gIII encompassing residues 249 through 406.

In one library, all possible residue combinations were allowed for VEGF 1–109 at positions 18, 21, 22, and 25 (by using oligonucleotides that changed target codons to NNS sequences, where N=G, A, T or C, and S=C or G), and change was allowed at 40% probability for position 17 (by enforcing a 70% probability of wild-type and a 10% probability of each of the three other base types for each base in the target codon).

The following oligonucleotides were used to change target codons to NNS sequences:

L-528: CAC GAA GTG GTG AAG TTC NNS GAT GTC NNS NNS CGC AGC NNS TGC CAT CCA ATC GAG (SEQ ID NO:1)

L-530: GGG GGC TGC TGC AAT NNS GAG NNS NNS GAG TGT GTG CCC ACT (SEQ ID NO:2).

In the second library, all possible residue combinations were allowed for VEGF 1–109 at positions 63, 65, and 66, and change was allowed at 40% probability for position 64.

In the third library, all possible residue combinations were allowed for VEGF (1–109) at positions 47 and 48, and change was allowed at 50% probability for positions 43 and 46. In the fourth library, all possible residue combinations were allowed for VEGF (1–109) at positions 63, 65, and 66, and change was allowed at 50% for position 64.

To generate KDR-selective variants, the mutated regions were divided into five groups as shown, and the first four were used to construct libraries for subsequent phage display selections. Residues marked with an asterisk (*) were "soft randomized" for a 50% bias towards wild-type, and residues marked with two asterisks were "hard randomized" (see FIG. 7, infra).

Synthesis of Heteroduplex DNA

Heteroduplex DNA was synthesized according to a procedure adapted from Kunkel et al., *Meth. Enzym.* 204: 125–139 (1991). Through this method, a mutagenic oligonucleotide was incorporated into a biologically active, covalently closed circular DNA (CCC-DNA) molecule. The procedure was carried out according to the following steps.

First, the oligonucleotides described above were 5'-phosphorylated. This was done by combining in an eppendorf tube 2 µg oligonucleotide, 2 µl 10× TM buffer (500 mM Tris-HCl, 100 mM MgCl$_2$, pH 7.5), 2 µl 10 mM ATP, and 1 µl 100 mM DTT, and then adding water to a total volume of 20 µl. Twenty units of T4 polynucleotide kinase (Weiss units) were added to the mixture and incubated for 1 hour at 37° C.

Next, each 5'-phosphorylated oligonucleotide was annealed to a phagemid template (single-strand DNA purified from a dut-/ung- *E. coli* strain CJ-236). This was done by first combining 1 µg single strand DNA template, 0.12 µg phosphorylated oligonucleotide, and 2.5 µl 10× TM buffer (500 mM Tris-HCl, 100 mM $MgCl_2$, pH 7.5), adding water to a total volume of 25 µl. The DNA quantities provided an oligonucleotide to template molar ratio of 3:1, assuming that the oligonucleotide to template length ratio is 1:100. The mixture was incubated at 90° C. for 2 minutes, then incubated at 50° C. for 3 minutes, and then incubated at 20° C. for 5 minutes.

Each 5'-phosphorylated oligonucleotide was then enzymatically extended and ligated to form a CCC-DNA molecule by adding the following reagents to the annealed mixture: 1 µl 10 mM ATP, 1 µl 25 mM dNTPs, 1.5 µl 100 mM DTT, 3 units T4 DNA ligase, and 3 units T7 DNA polymerase. The mixture was then incubated at 20° C. for at least 3 hours.

The DNA was purified by ethanol precipitation and resuspended in 15 µl of water.

*E. coli* Electroporation

The library phage were produced in a supressor strain of *E. coli* known as *E. coli* XL1-blue (Stratagene, LaJolla, Calif.) by *E. coli* electroporation. For electroporation, purified heteroduplex DNA first was chilled in a 0.2-cm gap electroporation cuvet on ice, and a 100 µl aliquot of electrocompetent *E. coli* XL1-blue was thawed on ice. The *E. coli* cells were added to the DNA and mixed by pipetting several times.

The mixture was transferred to the cuvet and electroporated using a Gene Pulser (Bio-rad, Hercules, Calif.) with the following settings: 2.5 kV field strength, 200 ohms resistance, and 25 mF capacitance. Immediately thereafter, 1 ml of SOC media (5 g bacto-yeast extract, 20 g bacto-tryptone, 0.5 g NaCl, 0.2 g KCl; add water to 1 liter and adjust pH to 7.0 with NAOH; autoclave; then add 5 mL of autoclaved 2 M $MgCl_2$ and 20 mL of filter sterilized 1 M glucose) was added and the mixture was transferred to a sterile culture tube and grown for 30 minutes at 37° C. with shaking.

To determine the library diversity, serial dilutions were plated on 2YT (10 g bacto-yeast extract, 16 g bacto-tryptone, 5 g NaCl; add water to 1 liter and adjust pH to 7.0 with NaOH; autoclaved) plates (supplemented with 50 µg/ml ampicillin). Additionally, the culture was transferred to a 250-ml baffled flask containing 25 ml 2YT, 25 mg/ml ampicillin, M13-VCS ($10^{10}$ pfu/mL) (Stratagene, LaJolla, Calif.), and incubated overnight at 37° C. with shaking.

The culture was then centrifuged for 10 minutes at 10 krpm, 2° C., in a Sorvall GSA rotor (16000 g). The supernatant was transferred to a fresh tube and 1/5 volume of PEG-NaCl solution (200 g/L PEG-8000, 146 g/L NaCl; autoclaved) was added to precipitate the phage. The supernatant/PEG-NaCl solution was incubated for 5 minutes at room temperature and centrifuged again to obtain a phage pellet.

The supernatant was decanted and discarded. The phage pellet was recentrifuged briefly and the remaining supernatant was removed and discarded. The phage pellet was resuspended in 1/20 volume of PBT buffer (PBS, 0.2% BSA, 0.1% Tween 20), and insoluble matter was removed and discarded by centrifuging the resuspended pellet for 5 minutes at 15 krpm, 2° C., in a SS-34 rotor (27000 g). The remaining supernatant contained the phage.

The supernatant was saved and used for sorting VEGF variants by their binding affinities. By producing the phage in a suppressor strain of *E. coli*, VEGF (1–109) variants-gIII fusion protein were expressed and displayed on the phage surface, allowing the phage to bind to KDR and/or Flt-1 receptors.

Affinity Sorting of the Libraries

Each library was sorted for binding to KDR (1–3) monomer using a competitive binding technique similar to a method used by H. Jin, *J. Clin. Invest.*, 98: 969 (1996), and shown to be useful for generating receptor-selective variants.

To conduct the competitive binding technique, each library was sorted for binding to immobilized KDR (1–3) monomer (Genentech, South San Francisco, Calif.) in the presence of a high concentration (100 nM) of competing Flt-1 (1–3) monomer (Genentech, Inc.) in solution. This was accomplished by first coating Maxisorp immunoplate wells (Nalge Nunc International, Rochester, N.Y.) with 80 µl per well of 2–5 µg/ml of KDR (1–3) monomer in coating buffer (50 mM sodium carbonate at pH 9.6) and incubating overnight at 4° C. The number of wells required depends on the diversity of the library. The coating solution was removed and blocked for 1 hour with 200 µl of 0.2% BSA in PBS. At the same time, an equal number of uncoated wells were blocked as a negative control.

The wells were washed eight times with PT buffer (PBS, 0.05% Tween 20) to remove the block buffer. Aliquots of 100 µl of library phage solution ($10^{12}$ phage/ml) in PBT buffer (PBS, 0.2% BSA, 0.1% Tween 20) were then added to each of the coated and uncoated wells. The Flt-1 (1–3) monomer was added with the phage solution. The wells were incubated at room temperature for 2 hours with gentle shaking.

The wells were then washed 10 times with PT buffer (PBS, 0.05% Tween 20) to remove the phage solution and any Flt-1-bound phage. KDR-bound phage was eluted from the wells by incubating the wells with 100 µl of 0.2 mM glycine at pH 2 for 5 minutes at room temperature. To collect the KDR-bound phage, the glycine solution was transferred to an eppendorf tube and neutralized with 1.0 M Tris-HCl at pH 8.0.

The KDR-bound phage were then repropagated by adding half of the eluted phage solution to 10 volumes of actively growing *E. coli* XL1-blue ($OD_{600}$<10) and incubating for 30 minutes at 37° C. with shaking. The serial dilutions of the culture were then plated on 2YT/amp plates (2YT being supplemented with 50 mg/ml ampicillin) to determine the number of phage eluted. This was determined for both the wells coated with KDR (1–3) monomer and the uncoated control wells.

The culture from the plates was transferred to 10 volumes of 2YT/amp/VCS (2 YT being supplemented with 50 mg/ml ampicillin and $10^{10}$ pfu/ml M13-VCS) and incubated overnight at 37° C. with shaking. The phage were then isolated.

The phage that were repropagated were again sorted for binding to immobilized KDR (1–3) monomer in the presence of a high concentration (100 nM) of competing Flt-1 (1–3) monomer, followed by washing away the Flt-1-bound phage and repropagating the KDR-bound phage. The affinity sort procedure was monitored by calculating the enrichment ratio and was repeated until the enrichment ratio reached a maximum (about 5 to 6 sorting cycles).

The enrichment ratio is the number of phage eluted from a well coated with KDR (1–3) monomer divided by the number of phage binding to an uncoated control well. A ratio greater than one is usually indicative of phage binding specifically to the KDR (1–3) protein, thereby indicating resistance to binding to added Flt-1 (1–3) monomer. When the enrichment ratio reached a maximum, individual clones were analyzed for specific binding.

Phage ELISA

Specific binding of phage having VEGF 1–109 variant-gIII protein on its surface to the KDR (1–3) monomer was measured using a phage ELISA according to Muller et al., *PNAS*, 94: 7192 (1997). For the phage ELISA, microtiter plates (Maxisorp, Nunc Immunoplate, Nalge Nunc International, Rochester, N.Y.) were coated with purified KDR (1–3) monomer or Flt-1 (1–3) monomer (5 ug/ml) in 50 mM sodium carbonate at pH 9.6 and incubated at 4° C. overnight. The plates were blocked with 0.5% BSA. Next, serial dilutions of VEGF 1–109 variants together with a subsaturating concentrating of competing receptor (KDR (1–3) monomer or Flt-1 (1–3) monomer) were added to wells in 100 ul of binding buffer (PBS, 0.5% Tween20, 0.5% BSA). After equilibrium, the plates were washed, and the bound phagemid were stained with horseradish peroxidase-conjugated anti-M13 antibody (Pharmacia Biotech, Piscataway, N.J.), following manufacturer instructions. Affinities (EC50) were calculated as the concentration of competing receptor that resulted in half-maximal phagemid binding.

The sequences of VEGF 1–109 variants which were obtained from the affinity sorting and which showed resistance to Flt-1 (1–3) monomer were determined from the sequence of the phagemid cDNA.

Purification of VEGF 1–109 Variants

VEGF 1–109 variant proteins were isolated as retractile bodies from the shake flask culture of *E. coli* (27c7). The refolding of the mutant proteins was performed as described by Yihai et al., *J. Biol. Chem.*, 271: 3154–3162 (1996). The variants were mixed and unfolded with 6 M guanidine HCL plus 1 mM oxidized glutathione at pH 6, and dialyzed against 10 volumes of 2 M urea with 2 mM reduced glutathione and 0.5 mM of oxidized glutathione in 20 mM Tris-HCL at pH 8 for 10 hours. Urea was removed by dialyzing slowly against 20 volumes of 20 mM Tris-HCL (pH 8) overnight at 4° C. Each of the variants was purified further by anion exchange (Pharmacia HiTrap Q, 1 ml) (Pharmacia Biotech, Piscataway, N.J.), to remove traces of misfolded monomer. The identity of the resulting pure variants was confirmed by SDS-PAGE and mass spectrometry.

Table 2 shows the VEGF variant identifier name, the amino acid substitutions introduced, and the codon encoding the respective substituted amino acids. The asterisk (*) next to certain variant identifiers (such as LK-VRB-1s) indicates various VEGF variants which demonstrated particularly preferred binding affinities and/or biological activities. The variant identifiers which contain an "s" (such as LK-VRB-1s) indicate VEGF variant polypeptides which consisted of the 1–109 truncated form of VEGF and contained the recited mutations provided in the Table. The variant identifiers which contain an "f" (such as LK-VRB-1f) indicate VEGF variant polypeptides which consisted of the full length 1–165 form of VEGF and contained the recited mutations provided in the Table. The naming and identification of the mutations in the variant sequences is in accord with naming convention. For example, for the first entry in Table 2, the mutation is referred to as "M18E". This means that the 18 position of the native VEGF sequence (using the numbering in the amino acid sequence for native human VEGF as reported in Leung et al., supra and Houck et al., supra) was mutated so that the native methionine (M) at that position was substituted with a glutamic acid (E) residue to prepare the VEGF variant. The column in Table 2 referred to as "Nucleotide Sequence" provides the respective codons coding (5'→3') for each of the respective amino acid mutations. For example, for the first entry in Table 2, the M18E mutation is coded by the codon "GAG".

TABLE 2

VEGF Variants and Corresponding Mutations

| Variant Identifier | Amino Acid Mutation | Nucleotide Sequence |
|---|---|---|
| LK-VRB-1s* | M18E/Y21L/Q22R/Y25S | GAG/CTC/CGG/AGC |
| LK-VRB-2s* | D63S/G65M/L66R | AGC/ATG/CGC |
| LK-VRB-3s | F17I/M18E/Y21F/Q22K/Y25S | ATT/GAG/TTC/AAG/AGC |
| LK-VRB-4s | F17I/M18E/Y21F/Q22E/Y25I | ATC/GAG/TTC/GAG/CAC |
| LK-VRB-5s | D63S/L66R | AAG/CAG |
| LK-VRB-6s | D63S/G65A/L66T | AAG/GGC/ATG |
| LK-VRB-7s* | M18E/D63S/G65M/L66R | GAG/AGC/ATG/CGC |
| LK-VRB-8s* | Y21L/D63S/G65M/L66R | CTC/AGC/ATG/CGC |
| LK-VRB-9s | Q22R/D63S/G65M/L66R | CGG/AGC/ATG/CGC |
| LK-VRB-10s | Y25S/D63S/G65M/L66R | AGC/AGC/ATG/CGC |
| LK-VRB-11s | M18E/Y21L/ D63S/G65M/L66R | GAG/CTC/ AGC/ATG/CGC |
| LK-VRB-12s | M18E/Q22R/ D63S/G65M/L66R | GAG/CGG/ AGC/ATG/CGC |
| LK-VRB-13s | M18E/Y25S/ D63S/G65M/L66R | GAG/AGC/ AGC/ATG/CGC |
| LK-VRB-14s | Y21L/Q22R/ D63S/G65M/L66R | CTC/CGG/ AGC/ATG/CGC |
| LK-VRB-15s | Y21L/Y25S/ D63S/G65M/L66R | CTC/AGC/ AGC/ATG/CGC |
| LK-VRB-16s | Q22R/Y25S/ D63S/G65M/L66R | CGG/AGC/ AGC/ATG/CGC |
| LK-VRB-17s | M18E/Y21L/Q22R/ D63S/GG5M/L66R | GAG/CTC/GAG/ AGC/ATG/CGC |
| LK-VRB-18s | M18E/Q22R/Y25S/ D63S/G65M/L66R | GAG/CGG/AGC/ AGC/ATG/CGC |
| LK-VRB-19s | M18E/Q22R/Y25S/ D63S/G65M/L66R | GAG/CGG/AGC/ AGC/ATG/CGC |
| LK-VRB-20s | Y21L/Q22R/Y25S/ D63S/G65M/L66R | CTC/CGG/AGC/ AGC/ATG/CGC |
| LK-VRB-21s | D63S/ M18E/Y21L/Q22R/Y25S | TCC/ GAG/CTC/CGG/AGC |
| LK-VRB-22s | G65M/ M18E/Y21L/Q22R/Y25S | ATG/ GAG/CTC/CGG/AGC |
| LK-VRB-23s | L66R/ M18E/Y21L/Q22R/Y25S | AGG/ GAG/CTC/CGG/AGC |
| LK-VRB-24s | D63S/G65M/ M18E/Y21L/Q22R/Y25S | TCC/ATG/ GAG/CTC/CGG/AGC |
| LK-VRB-25s | D63S/L66R/ M18E/Y21L/Q22R/Y25S | TCC/AGG/ GAG/CTC/CGG/AGC |
| LK-VRB-26s | G65M/L66R/ M18E/Y21L/Q22R/Y25S | ATG/AGG/ GAG/CTC/CGG/AGC |
| LK-VRB-27s | M18E/Y21L/Q22R/Y25S/ D63S/G65M/L66R | GAG/CTC/CGG/AGC/ AGC/ATG/CGC |
| LK-VRB-1f | M18E/Y21L/Q22R/Y25S | GAG/CTC/CGG/AGC |
| LK-VRB-2f | D63S/G65M/L66R | AGC/ATG/CGC |

Example 2

Binding of VEGF Variants to KDR Receptor

The binding of VEGF (1–109) variants and VEGF165 variants (described in Example 1) to KDR receptor was evaluated by measuring the ability of the variants to inhibit binding of biotinylated native VEGF (8–109) to KDR receptor. The VEGF variants evaluated contained the mutations shown in Table 2.

Receptor binding assays were performed in 96-well immunoplates (Maxisorp, Nunc-Immunoplate, Nalge Nunc International, Rochester, N.Y.). Each well was coated with 100 μl of a solution containing 8 μg/ml of a monoclonal antibody to KDR known as MAKD5 (Genentech, South San Francisco, Calif.) in 50 mM carbonate buffer at pH 9.6 and incubated at 4° C. overnight. The supernatant was discarded, the wells were washed three times in washing buffer (0.05% Tween 20 in PBS), and the plate was blocked (150 μl per well) with block buffer (0.5% BSA, 0.01% thimerosal in PBS) at room temperature for one hour. The supernatant was discarded, and the wells were washed.

Serially diluted native VEGF(8–109), native VEGF (1–165), native VEGF (1–109) variants, or VEGF165 variants (0.16–168 nM in monomer) were incubated with biotinylated native VEGF (8–109) (84 nM) and KDR (1–3) (1 μg/ml) for 2 hours at room temperature in assay buffer (0.5% BSA, 0.05% Tween 20 in PBS). Aliquots of this mixture (100 μl) were added to the precoated microtiter wells and the plate was incubated for 1 hour at room temperature. The complex of KDR (1–3) and biotinylated native VEGF that was bound to the microtiter plate was detected by incubating the wells with peroxidase-labeled streptavidin (0.2 mg/ml, Sigma, St. Louis, Mo.) for 30 minutes at room temperature. The wells were then incubated with 3, 3', 5,5'-tetramethyl benzidine (0.2 gram/liter; Kirkegaard & Perry Laboratories, Gaithersburg, Md.) for about 10 minutes at room temperature. Absorbance was read at 450 nm on a Vmax plate reader (Molecular Devices, Menlo Park, Calif.).

Titration curves were fit with a four-parameter nonlinear regression curve-fitting program (KaleidaGraph, Synergy Software, Reading, Pa.). Concentrations of VEGF variants corresponding to the midpoint absorbance of the titration curve of the native VEGF (8–109) were calculated and then divided by the concentration of the native VEGF corresponding to the midpoint absorbance of the native VEGF titration curve. (See FIG. 2)

The binding affinities determined for the VEGF (1–109) variants and VEGF165 variants are shown in Table 3. Many of the VEGF variants exhibited binding to KDR receptor that was within about two-fold of the binding of native VEGF (8–109).

Example 3

Binding of VEGF Variants to Flt-1 Receptor

The binding of, the VEGF (1–109) variants and VEGF165 variants (described in Example 1) to Flt-1 receptor was evaluated by measuring the ability of the variants to inhibit binding of biotinylated native VEGF (8–109) to Flt-1 receptor. The VEGF variants evaluated contained the mutations shown in Table 2.

Receptor binding assays were performed in 96-well immunoplates (Maxisorp, Nunc-Immunoplate, Nalge Nunc International, Rochester, N.Y.). Each well was coated with 100 μl of a solution containing 2 μg/ml of rabbit F(ab')2 to human IgG Fc (Jackson ImmunoResearch, West Grove, Pa.) in 50 mM carbonate buffer at pH 9.6 and incubated at 4° C. overnight. The supernatant was then discarded, the wells were washed three times in washing buffer (0.05% Tween 20 in PBS), and the plate was blocked (150 μl per well) with block buffer (0.5% BSA, 0.01% thimerosal in PBS) at room temperature for one hour. The supernatant was discarded, and the wells were washed.

The wells were filled with 100 μl of a solution containing Flt-IgG (a chimeric Flt-human Fc molecule) at 50 ng/ml in assay buffer (0.5% BSA, 0.05% Tween 20 in PBS). The wells were incubated at room temperature for 1 hour and then washed three times in wash buffer (0.05% Tween 20 in PBS).

Serially diluted native VEGF(8–109), native VEGF165, VEGF (1–109) variants, or VEGF165 variants (0.03–33 nM in monomer) were mixed with biotinylated native VEGF (8–109) (0.21 nM) or biotinylated native VEGF165 (0.66 nM). Aliquots of the mixture (100 μl) were added to the precoated microtiter wells and the plate was incubated for 2 hours at room temperature. The complex of Flt-IgG and biotinylated native VEGF that was bound to the microtiter plate was detected by incubating the wells with peroxidase-labeled streptavidin (0.2 mg/ml, Sigma, St. Louis, Mo.) for 30 minutes at room temperature. The wells were then incubated with 3, 3', 5,5'-tetramethyl benzidine (0.2 g/liter, Kirkegaard & Perry Laboratories, Gaithersburg, Md.) for about 10 minutes at room temperature. Absorbance was read at 450 nm on a Vmax plate reader (Molecular Devices, Menlo Park, Calif.).

Titration curves were fit with a four-parameter nonlinear regression curve-fitting program (KaleidaGraph, Synergy Software, Reading, Pa.). Concentrations of VEGF variants corresponding to the midpoint absorbance of the titration curve of the native VEGF (8–109) were calculated and then divided by the concentration of the native VEGF corresponding to the midpoint absorbance of the native VEGF titration curve.

The binding affinities determined for the VEGF (1–109) variants and VEGF165 variants are shown in Table 3. Many of the VEGF variants exhibited binding to Flt-1 receptor that was more than 2,000-fold less than the binding of native VEGF (8–109). The relative binding affinity data reported in Table 3 for certain VEGF variants (for instance, LK-VRB-7s* and LK-VRB-8s*) to FLT-1 receptor is not reported in nM values since the amount of detectable binding was beyond the sensitivity of the ELISA assay.

TABLE 3

|  | Relative Binding Affinity | |
| --- | --- | --- |
| Variant Identifier | KDR Receptor | FLT-1 Receptor |
| LK-VRB-1s* | 1 nM/1 | 2700 nM/6000 |
| LK-VRB-2s* | 1 nM/1 | >400 nM/>1000 |
| LK-VRB-3s | 1 nM/1 | 170 nM/400 |
| LK-VRB-4s | 1 nM/1 | 100 nM/200 |
| LK-VRB-5s | 1 nM/1 | 233 nM/550 |
| LK-VRB-6s | 0.5 nM/0.5 | 4 nM/10 |
| LK-VRB-7s* | 1 nM/1 | />15000 |
| LK-VRB-8s* | 0.5 nM/0.5 | />21000 |
| LK-VRB-9s | 0.5 nM/0.5 | /300 |
| LK-VRB-10s | 0.5 nM/0.5 | />2400 |
| LK-VRB-11s | 2 nM/2 | />14000 |
| LK-VRB-12s | 0.4 nM/0.4 | />5600 |
| LK-VRB-13s | 14 nM/14 | />14000 |
| LK-VRB-14s | 0.5 nM/0.5 | />2900 |
| LK-VRB-15s | 2 nM/2 | />21000 |
| LK-VRB-16s | 0.6 nM/0.6 | />1400 |

TABLE 3-continued

| | Relative Binding Affinity | |
|---|---|---|
| Variant Identifier | KDR Receptor | FLT-1 Receptor |
| LK-VRB-17s | 3 nM/130 | />1900 |
| LK-VRB-18s | 130 nM/130 | />3900 |
| LK-VRB-19s | 7 nM/7 | />35000 |
| LK-VRB-20s | 2 nM/2 | />10000 |
| LK-VRB-21s | 3 nM/3 | />5600 |
| LK-VRB-22s | 4 nM/4 | />30 |
| LK-VRB-23s | 11 nM/11 | />8500 |
| LK-VRB-24s | 10 nM/10 | />18000 |
| LK-VRB-25s | 4 nM/4 | />12000 |
| LK-VRB-26s | 23 nM/23 | />25000 |
| LK-VRB-2f | 1 nM/1 | 19 nM/70 |
| Compare Native VEGF (8–109) | 1 nM/1 | 0.42 nM/1 |

Example 4

Induction of KDR Receptor Phosphorylation by VEGF (1–109) Variants

To determine the activity of the VEGF variants, the ability of the variants to induce phosphorylation of the KDR receptor was measured in a KIRA assay. The VEGF variants evaluated contained the mutations found in Table 2. Specifically, the following VEGF (1–109) variants were studied: LK-VRB-1s*; LK-VRB-2s*; LK-VRB-3s; LK-VRB-4s; LK-VRB-5s; and LK-VRB-6s.

Serially diluted VEGF (1–109) variants (0.01–10 nM) were added to CHO cells that express the KDR receptor with a gD tag at the N-terminus (Genentech, South San Francisco, Calif.). Cells were lysed by 0.5% Triton-X100, 150 mM NaCl, 50 mM Hepes at pH 7.2, and phosphorylated gD-KDR receptor in the lysate was quantified by conducting an ELISA.

For the ELISA, 96-well immunoplates (Maxisorp, Nunc-Immunoplate, Nalge Nunc International, Rochester, N.Y.) were used. Each well was coated with 100 µl of a solution containing 1 µg/ml of a mouse monoclonal antibody to gD known as 3C8 (Genentech, South San Francisco, Calif.) in 50 mM carbonate buffer at pH 9.6 and incubated overnight at 4° C. The supernatant was discarded, the wells were washed three times in washing buffer (0.05% Tween 20 in PBS), and the plate was blocked (150 µl per well) in block buffer (0.5% BSA, 0.01% thimerosal in PBS) for 1 hour at room temperature. The supernatant was then discarded, and the wells were washed.

Aliquots of the lysate (100 µl) were added to the precoated wells and incubated for 2 hours at room temperature. The phosphorylated gD-KDR receptor was detected by incubating the wells with biotinylated monoclonal antibody to phosphotyrosine known as 4G10 (0.05 mg/ml) (Upstate Biotechnology, Lake Placid, N.Y.) for 2 hours at room temperature followed by incubating the wells with peroxidase-labeled streptavidin (0.2 mg/ml, Sigma, St. Louis, Mo.) for 1 hour at room temperature. The wells were then incubated with 3, 31, 5, 5'-tetramethyl benzidine (0.2 g/liter, Kirkegaard & Perry Laboratories, Gaithersburg, Md.) for about 15–20 minutes at room temperature. Absorbance was read at 450 nm on a Vmax plate reader (Molecular Devices, Menlo Park, Calif.).

Titration curves were fit with a four-parameter nonlinear regression curve-fitting program (KaleidaGraph, Synergy Software, Reading, Pa.). Concentrations of VEGF variants corresponding to the midpoint absorbance of the titration curve of the native VEGF (8–109) were calculated and then divided by the concentration of the native VEGF corresponding to the midpoint absorbance of the native VEGF titration curve. (FIG. 3)

The phosphorylation-inducing activity of the VEGF variants are provided in Table 4. The VEGF variants generally exhibited phosphorylation-inducing activity that was within two-fold of the activity of native VEGF (8–109).

TABLE 4

Induction of KDR Receptor Phosphorylation By VEGF (1–109) Variants

| Variant Identifier | Phosphorylation-Inducing Activity |
|---|---|
| LK-VRB-1s* | 1 nM/0.5 |
| LK-VRB-2s* | 2 nM/1 |
| LK-VRB-3s | 2 nM/1 |
| LK-VRB-4s | 1 nM/0.5 |
| LK-VRB-5s | 1 nM/0.5 |
| LK-VRB-6s | 1 nM/0.5 |
| Compare Native VEGF (8–109) | 2 nM/1 |

Example 5

Endothelial Cell Proliferation Assay

The mitogenic activity of VEGF (1–109) or VEGF165 variant's (as well as one VEGF165 variant, LK-VRB-2f) was determined by using human umbilical vein endothelial cells (HUVEC) (Cell Systems, Kirkland, Wash.) as target cells. The VEGF variants evaluated contained the mutations in Table 2. Specifically, the following VEGF (1–109) variants were studied: LK-VRB-1s*; LK-VRB-2s*; LK-VRB-7s*; and LK-VRB-8s*.

HUVEC is a primary cell line that is maintained and grown with growth factors such as acidic FGF in CS-C Complete Growth media (Cell Systems, Kirkland, Wash.). To prepare for the assay, an early passage (less than five passages) of the cells was washed and seeded in 96-well plates (3000 cells in 100 µl per well) and fasted in CS-C media without any growth factors but supplemented with 2% Diafiltered Fetal Bovine Serum (GibcoBRL, Gaithersburg, Md.) for 24 hours at 37° C. with 5% $CO_2$ incubator before replacing with fresh fasting media. VEGF variants at several concentrations (about 10 nM to 0.01 nM) diluted in the same fasting media were added to the wells to bring the volume to 150 µl per well and incubated for 18 hours.

To measure the DNA synthesis induced by the VEGF variants, $^3$H-thymidine (Amersham Life Science, Arlington Heights, Ill.) was added to each well at 0.5 µCi per well and incubated for another 24 hours for the cells to take up the radioactivity. The cells were then harvested onto another 96-well filter plate and the excess label was washed off before loading the plates on the Topcount (Packard, Meriden, Conn.).

The cells were counted by Topcount. The measured counts per minute (CPM) were plotted against the concentration of individual variants to compare their activities. (FIG. 4)

The cell proliferation capabilities of the VEGF variants are shown in Table 5. The VEGF variants generally exhibited cell proliferation capability that was within two-fold of the capability of native VEGF (8–109).

TABLE 5

Mitogenic Activity of VEGF (1–109) Variants

| Variant Identifier | Endothelial Cell Proliferation Activity |
|---|---|
| LK-VRB-1s* | 0.1 nM/0.2 |
| LK-VRB-2s* | 0.05 nM/0.1 |
| LK-VRB-7s* | 0.5 nM/1 |
| LK-VRB-8s* | 0.5 nN/1 |
| LK-VRB-2f | 0.05 nM/0.1 |
| Compare Native VEGF (8–109) | 0.5 nM/1 |

Example 6

RIA Assay to Determine Binding of VEGF Variants to KDR and FLT-1 Receptors

An RIA assay was conducted essentially as described in Muller et al., *PNAS*, 94:7192–7197 (1997) to examine relative binding affinities of several of the VEGF variants (described in Table 2) to the KDR receptor and FLT-1 receptor, as compared to native VEGF 165 or native VEGF (8–109). The results are shown below in Table 6.

TABLE 6

Relative Binding Affinity

| Variant Identifier | KDR Receptor | FLT-1 Receptor |
|---|---|---|
| Native VEGF 165 | 1 (97 pM) | 1 (37 pM) |
| Native VEGF (8–109) | 12 | 29 |
| LK-VRB-1f | 8 | 1700 |
| LK-VRB-1s* | 20 | 14,000 |
| LK-VRB-2f | 1 | 2400 |
| LK-VRB-2s* | 2 | 27,000 |

Example 7

Binding of VEGF Variants to KDR- or FLT-1-Transfected Cells

The binding properties of LK-VRB-2s* (see Example 1, Table 2) were further examined in a receptor-transfected cell binding assay. KDR or Flt-1 transfected NIH3T3 cells were prepared as described by Fuh et al., *J. Biol. Chem.*, 273: 11187–11204 (1998). The transfected cells were maintained in F12 media supplemented with 10% FBS and 400 ug/ml G418 (GibcoBRL). For the binding assays, the cells were plated in 12-wells plates at 1×10$^6$/well to reach confluency next day. The cells were then washed and blocked in Hank's buffered saline (HBS) with 1% BSA for one hour before adding $^{125}$I-VEGF (1–109) (prepared by standard chloramine-T methods) and increasing concentrations of unlabeled VEGF variants. 50 pM and 10 pM of labeled VEGF (1–109) was used for KDR and Flt-1 cell binding, respectively. The plates were incubated at 4° C. for three hours and then washed two times with HBS with 0.5% BSA. The bound, labeled VEGF was collected by solubilizing the washed cells with 1N NaOH, and then counted in a gamma-counter (Isodata, ICN).

As shown in FIG. 5, LK-VRB-2s* showed binding to the transfected cells expressing KDR similar to native VEGF binding. The LK-VRB-2s* however, exhibited about a 200-fold reduced binding to the cells transfected with Flt-1 (see FIG. 6).

Example 8

Generation and Selection of a Flt-1 Specific VEGF Variant

An alanine scan (Wells, *Methods Enzmmol.*, 202:390–411 (1991)) was used to define the relative importance for KDR vs. Flt-1 binding of individual VEGF residues. The residues selected for mutagenesis included the 22 contact residues observed in the crystal structure of the complex between the receptor-binding domain of VEGF and domain 2 of Flt-1 (Wiesmann et al., *Cell*, 91:695–704 (1997)), as well as Phe 47 and Glu 64, which had previously been identified as KDR-binding determinants (Muller et al., *Proc. Natl. Acad. Sci.*, 94:7192–7197 (1997)). Site-directed mutagenesis was performed using the method of Kunkel et al., *Methods Enzmmol.*, 204:125–139 (1991) in the background of the receptor-binding domain (residues 1 to 109) of VEGF. All mutations were verified by DNA sequencing. The following VEGF residues were individually mutated to alanine: Lys 16, Phe 17, Met 18, Tyr 21, Gln 22, Tyr 25, Ile 43, Ile 46, Phe 47, Lys 48, Asp 63, Glu 64, Gly 65, Leu 66, Gln 79, Met 81, Ile 83, His 86, Gln 89, Ile 91, Lys 101, Glu 103, Arg 105, Pro 106. These residues were individually mutated to alanine in the background of the receptor-binding domain of VEGF (residues 1 to 109: Keyt et al., *J. Biol. Chem.*, 271:7788–7795 (1996); Muller et al., *Proc. Natl. Acad. Sci.*, 94:7192–7197 (1997)).

Each mutant protein was produced and purified to homogeneity, and an enzyme-linked immunosorbant assay (ELISA) was used to determine binding affinities for domains 1 to 3 of KDR and Flt-1 (these three domains contain the entire VEGF-binding site; Wiesmann et al., *Cell*, 91:695–704 (1997); Fuh et al., *J. Biol. Chem.*, 273:11197–11204 (1998)). For the ELISA, microtiter plates were coated with purified VEGF (8–109) (at 5 μg/ml) in 50 mM sodium carbonate (pH 9.6) at 4° C. overnight. Plates were blocked with 0.5% BSA, and serial dilutions of competing VEGF alanine mutants and a sub-saturating concentration (100 pM) of biotin-labeled receptor (KDR(1–3) or Flt1(1–3)) were added to wells in 100 μl of binding buffer (0.5% Tween20, 0.5% BSA in PBS). After 1 hour, the plates were washed, and the bound protein stained with streptavidin horseradish peroxidase conjugate (Pharmacia) and assayed. Affinities were estimated as IC$_{50}$ values: the concentration of KDR(1–3) or Flt(1–3) that blocked 50% of protein binding.

The results of this analysis are shown in FIG. 7. Listed for each residue is the ratio of the IC$_{50}$ of the mutant to the IC$_{50}$ of the wild-type VEGF (8–109), representing the fold reduction in binding of the mutant compared to the wild-type protein. IC$_{50}$s for wild-type VEGF(8–109) are shown in parentheses. Residues shown in bold face were used to generate the Flt-1-selective variant.

The concurrent analysis of the VEGF mutants for Flt-1 binding shows a similar and overlapping receptor-binding region, predominately localized in the 20s helix and the 60s loop, the most important Flt-1-binding determinants being Phe 17, Tyr 21, Gln 22, and Leu 66 (FIG. 7). In contrast, mutation of the critical Flt-1-binding determinants also tended to significantly reduce affinity for KDR (FIG. 7).

A VEGF variant with high selectivity for the Flt-1 receptor was generated by combining four mutations that greatly affected KDR but not Flt-1 binding. Mutation to alanine of Ile 43, Ile 46, Gln 79 or Ile 83 showed that the side chains of these residues are critical for tight binding to KDR but unimportant for Flt-1-binding. A variant (referred to herein as "Flt-sel") was constructed with alanine substitutions at positions Ile 43, Ile 46, Gln 79 and Ile 83, using site directed mutagenesis methods (Kunkel et al., *Methods Enzymol.*, 204:125–139 (1991)). This particular Flt-sel variant can also be represented by the identifier, I43A/I46A/Q79A/I83A, in accordance with the nomenclature described in Example 1 above (and illustrated in Table 2). The corresponding codons for these four alanine substitutions at positions 43, 46, 79 and 83 are GCC/GCC/GCG/GCC, respectively (in accordance with the nomenclature described in Example 1 above and illustrated in Table 2).

Various assays were conducted to examine the properties and biological activities of the I43A/I46A/Q79A/I83A Flt-sel variant. For example, quantitative binding measurements were carried out using a soluble radio-immuno receptor-binding assay (RIA), as described in Example 6 above. In the assay, native VEGF(8–109) had affinities for KDR and Flt-1 of 0.5 nM and 0.4 nM, respectively (FIGS. 8A and 8B). Flt-sel was found to have at least 470-fold reduced KDR-binding affinity in this assay (FIG. 8A). Somewhat surprisingly, since small reductions in Flt-1-binding had been observed from the individual point mutants in the ELISA (described above), the Flt-sel variant's affinity for Flt-1 was essentially identical to that of the native protein (FIG. 8B).

The activity of the Flt-sel variant was also tested in the 3T3 transfected cell-binding assay described in Example 7. Consistent with the RIA data, Flt-sel showed no detectable binding to KDR-transfected 3T3 cells and slightly improved binding to Flt-1-transfected cells (FIGS. 5 and 6).

The activity of the Flt-sel variant was also tested in the KIRA assay described in Example 4. The results are shown in FIG. 9.

The activity of the Flt-sel variant was further tested in the HUVEC proliferation assay described in Example 5. The results are shown in FIG. 10.

Example 9

Matrix Metalloprotease 9 Assay

An assay that measures the secretion of matrix metalloprotease 9 following activation of Flt-1 expressed on human smooth aorta muscle cells was conducted (Wang and Keiser, *Circ. Res.*, 83:832–840 (1998)). Human aorta smooth muscle cells (ASMC) (Clonetics) were maintained in SM2 media (Clonetics) at 37° C. in 5% $CO_2$ and 95% ambient air in the presence of 10% fetal bovine serum in 6-well polystyrene plates (Becton-Dickinson). When, cells attained 90% confluence, they were growth-arrested for 24 hours in serum-free medium containing 0.2% bovine serum albumin (BSA). VEGF(1–109), PlGF (R & D Systems, Minneapolis, Minn.) or VEGF(1–109) variants (LK-VRB-2s* and Flt-sel (described above) were added at a final concentration of 40 ng/ml and the cells were cultured for an additional 24 hours in the serum-free media containing 0.2% BSA. Gelatinase in the conditioned media was then analyzed by zymography. Media were collected and concentrated, and 25 µl aliquots were mixed with 2× sample buffer without reducing agent or heating. Samples were loaded on a 10% polyacrylamide gel containing 0.1% gelatin (Novex, San Diego, Calif.) for electrophoresis. In addition to using regular molecular weight markers, the MMP-2 and -9 zymographic standards (Chemicon, Temecula, Calif.) were used as standards for gelatinases. After electrophoresis, proteins were renatured by incubation of the gels for 30 minutes at room temperature in Renaturing Buffer and in Developing Buffer (Novex) for overnight at 37° C. The gels were stained with 0.25% Coomassie Brilliant Blue (Sigma). Gelatinase activity was identified as lightly stained or clear bands following destaining.

The results are shown in FIG. 11. Shown is a representative zymogram of one of two independent experiments. Fold change represents the relative band density of the VEGF(1–109)-, VEGF(1–109) variants- or PlGF-treated groups versus the vehicle-treated (PBS) control. In contrast to LK-VRB-2s*, Flt-sel was fully active in this assay when compared to the activity of the native VEGF(1–109) or PlGF (FIG. 11).

Example 10

Activation of MAP Kinases

Assays were conducted to determine whether native VEGF, KDR-selective VEGF variant, or Flt-selective VEGF variant were capable of mediating mitogenic signaling.

Passage 4–7 HUVEC cells (Cell Systems, Kirkland, Wash.) were grown in Cell System's complete medium (AZ0-500) with 10% fetal calf serum and growth factors on gelatin-coated dishes and made quiescent by 14 hour starvation in 0.2% serum. Quiescent HUVEC cells were either left untreated or stimulated with native VEGF (1–165) or VEGF variants (a Flt-1 selective variant comprising a full length 165 sequence and containing the alanine amino substitutions I43A/I46A/Q79A/I83A described for the "short form" (1–109) Flt-sel in Example 8 above; or the KDR-selective variant (also comprising full length 165 sequence) referred to as LK-VRB-2f (see Example 1; Table 2) (at, concentrations of either 50 ng/ml or 10 ng/ml) for 5 minutes. Both the native VEGF (1–165) and VEGF variants were expressed in *E. coli* and purified as described in Keyt et al., *J. Biol. Chem.*, 271:5638–5646 (1996). The HUVEC cells were then lysed in 0.5–1 ml RIPA buffer containing 0.1 mM sodium orthovanadate, 5 mM para-nitrophenylphosphate, 10 mM sodium fluoride, 0.5 micromolar okadaic acid and a protease inhibitor cocktail (Roche MB 1836145). Western blot analysis was then conducted, probing for phosphorylated ERK1 or ERK2 using anti-phospho ERK antiserum (Promega).

Activation by the KDR-selective VEGF variant, LK-VRB-2f, triggered phosphorylation of ERK1 and ERK2 in HUVEC cells (FIG. 12A). The extent of phosphorylation was indistinguishable from that obtained using native VEGF (1–165). The Flt-1 selective VEGF variant (at the highest concentration used) resulted in barely detectable phosphorylation of ERK2. The homodimeric VEGF variants utilized in this study are not expected to promote receptor heterodimer formation. Thus Flt-1 does not contribute to MAP kinase activation.

VEGF has previously been reported to stimulate the stress-activated, p38 MAP kinase [Rousseau et al., *Oncogene*, 15:2169–2177 (1997); Yu et al., *J. Cell. Phys.*, 178: 235–246 (1999)]. In order to analyze which VEGF receptor is involved, the phosphorylation status of p38 was examined after stimulation with native VEGF (1–165), Flt-1 selective variant, or LK-VRB-2f (described above).

Passage 4–7 HUVEC cells (Cell Systems, Kirkland, Wash.) were grown in Cell System's complete medium (AZ0-500) with 10% fetal calf serum and growth factors on gelatin-coated dishes and made quiescent by 14 hour starvation in 0.2% serum. Quiescent HUVEC cells were either left untreated or stimulated with native VEGF (1–165) or the VEGF variants (Flt-sel (full length 165 form) or LK-VRB-2f; both described above for the ERK1 and ERK2 assay) (at concentrations of either 50 ng/ml or 10 ng/ml) for 5 minutes. The cells were then lysed in 0.5–1 ml RIPA buffer containing 0.1 mM sodium orthovanadate, 5 mM para-nitrophenylphosphate, 10 mM sodium fluoride, 0.5 micromolar okadaic acid and a protease inhibitor cocktail (Roche MB 1836145). The phosphorylation state of p38 stress-activated MAP kinase was assessed with an anti-phospho p38 specific antiserum (NEB).

FIG. 12B demonstrates that the KDR-selective VEGF variant was able to stimulate p38 phosphorylation.

Example 11

KDR stimulates PI 3'-Kinase and PLC-Gamma Phosphorylation

PLC-gamma phosphorylation and activation has previously been implicated in VEGF signaling. PLC-gamma binding to both KDR [Dougher et al., Oncogene, 18:1619–1627 (1999); Cunningham et al., Biochem. Biophys. Res. Comm., 240:635–639 (1997))] and Flt-1 [Seetharam et al., Oncogene, 10:135–147 (1995); Sawano et al., Biochem. Biophys. Res. Comm., 238:487–491 (1997); Ito et al., J. Biol. Chem., 273:23410–23418 (1998)] has been reported.

In order to determine which VEGF receptor(s) are involved in PLC-gamma activation in primary endothelial cells, HUVEC cells were treated with native VEGF or VEGF receptor-selective variants and PLC-gamma phosphorylation was assessed after immunoprecipitation.

Passage 4–7 HUVEC cells (Cell Systems, Kirkland, Wash.) were grown in Cell System's complete medium (AZ0-500) with 10% fetal calf serum and growth factors on gelatin-coated dishes and made quiescent by 14 hour starvation in 0.2% serum. Quiescent HUVEC cells were either left untreated or stimulated with native VEGF (1–165) or VEGF variants (Flt-sel (full length 165 form) or LK-VRB-2f; described above in Example 10) (at concentrations of 20 ng/ml) for 5 minutes. The cells were then lysed in 0.5–1 ml RIPA buffer containing 0.1 mM sodium orthovanadate, 5 mM para-nitrophenylphosphate, 10 mM sodium fluoride, 0.5 micromolar okadaic acid and a protease inhibitor cocktail (Roche MB 1836145). PLC-gamma was then immunoprecipitated from whole cell lysates using monoclonal antibodies (Upstate Biotechnology) and analyzed for tyrosine phosphorylation (FIG. 13A) or lysates were immunoprecipitated with monoclonal antibodies against p85 PI 3'-kinase (purchased from Transduction Labs (P13020) and Neomarkers (MS424-P)) and tested for phosphotyrosine using phosphotyrosine antibodies PY20 or E120H (Transduction Labs) (FIG. 13B). Immunoprecipitation was conducted as follows. Protein A/G beads (Pierce) were blocked for nonspecific protein binding in 50 mM HEPES pH 7.2, 0.1% TX-100, 150 mM NaCl and 1 mg/ml ovalbumin for 30 minutes. Antibodies were precoupled in the same buffer for 1 hour at 4° C. with head over end rotation and beads were washed 3 times in lysis buffer. Beads were added to the lysates and rotated overnight. Beads were washed sequentially in 50 mM Tris pH 7.6, 150 mM NaCl, 1% TX-100, 1 mM $CaCl_2$; 50 mM Tris pH 7.6, 500 mM NaCl, 0.1% TX-100, 1 mM $CaCl_2$ and 50 mM Tris pH 7.6, 150 mM NaCl, 0.05% TX-100, 1 mM $CaCl_2$. Beads were then resuspended in 2× sample buffer and boiled. Supernatants were applied directly to 4–12% Tris-Glycine gradient gels (Novex).

As shown in FIG. 13A, both native VEGF and KDR-selective VEGF variant were able to stimulate PLC-gamma phosphorylation to a similar extent. The Flt-1 selective VEGF variant did not increase PLC-gamma phosphorylation over background levels, arguing against a role for Flt-1 in PLC-gamma activation in HUVEC cells.

PI 3'-kinase has been demonstrated to transmit survival signals through the activation of Akt in several cell types [Marte et al., Trends Biochem. Sci., 22:355–358 1997)]. VEGF also acts as a survival factor for endothelial cells and this signal requires PI-3' kinase and Akt kinase activity [Gerber et al., J. Biol. Chem., 273:30366–30343 (1998)]. In a variety of cell types, PI-3'kinase activity has been demonstrated to be involved in cytoskeletal changes following growth factor stimulation as well as cell migration [Wennstrom et al., Curr. Biol., 4:385–393 (1994)]. Therefore, the capacity of the VEGF proteins to cause phosphorylation of the p85 regulatory subunit of PI-3'kinase was assessed after immunoprecipitation. Only native VEGF and KDR-selective VEGF variant were capable of causing phosphorylation of the PI-3'kinase regulatory subunit, as shown in FIG. 13B.

Example 12

Effects on Endothelial Cell Migration

One of the central aspects of VEGF action on endothelial cells is its ability to act as a chemoattractant and stimulate the migration of endothelial cells. HUVEC cell migration was analyzed in a modified Boyden chamber assay as follows.

Falcon 8.0 micron filter inserts (Falcon 3097) were coated with type 1 collagen (VITROGEN, COHESION). HUVEC (obtained from Cell Systems, <passage 8) were grown in Cell Systems complete media (4ZO-500) with 10% FCS. Cells were trypsinized and transferred to EBM (Endothelial basal media, Clonetics) with 0.1% BSA for the assay. Cells were plated at $5\times10^4$ per upper chamber. Growth factors (VEGF (1–165); Flt-1 selective variant; LK-VRB-2f; described above in Example 10) were placed in the lower chamber (at the concentrations shown in FIGS. 14A and 14B) and inhibitors in the upper chamber. The assay was routinely an 18 hour assay at 37° C. For the LY294002 inhibitor experiments, cells were allowed to adhere for 30 minutes prior to addition of the inhibitor. 20 minutes after inhibitor addition, VEGF was added to the bottom well and the assay was allowed to proceed for only 4 hours to avoid the occurrence of apoptosis associated with the treatment of these primary cells with LY294002 (purchased from Biomol).

Cells were removed from the upper side of the membrane by scraping with a polyurethane swab and then the remaining cells on the bottom side of the membrane were fixed with methanol. Cells were stained with Yo-Pro Iodide nuclear stain (Molecular Probes) and counted under low power fluorescence using an Image-Pro cell recognition program.

FIG. 14A shows the effect of receptor-selective VEGF variants on HUVEC cells (at the indicated concentrations) in a modified Boyden chamber assay (experiments were performed in triplicate; error bars represent the standard error). In several independent experiments, native VEGF caused a 4–5 fold increase in HUVEC cell migration. The KDR-selective VEGF variant was as effective as the native VEGF in the promotion of HUVEC cell migration. The Flt-1 selective VEGF variant was unable to increase cell migration over background levels.

In order to determine the contribution of PI 3-kinase to endothelial cell migration, different concentrations of the inhibitor LY 294002 were added to the assay after the cells had been allowed to attach to the membrane. Due to the deleterious effects of PI 3'-kinase inhibition on endothelial cell survival a short-term assay was performed (as described above). FIG. 14B shows that at its highest concentration, LY 294002 caused a 56% inhibition of HUVEC cell migration. Thus, PI 3'-kinase activity contributes significantly to endothelial cell migration.

Example 13

Corneal Pocket Angiogenesis Assay

Assays were performed as described by Polyerini et al., *Methods Enzymol.*, 198:440–450 (1991) with the following modifications. Sprague-Dawley rats were anesthetized using a gas (isoflurane)/injectable ketamine (80 mg/kg)/xylazine (15 mg/kg) combination. The eyes were gently proptosed and secured in place using nontraumatic forceps. With a #15 blade, a 1.5 mm incision was made slightly below the center of the cornea. Using a micro spatula (ST80017, ASSI), the incision was carefully blunt-dissected through the stroma toward the outer canthus of the eye. A hydron coated pellet (2 mm×2 mm) containing growth factor (200 ng) (VEGF (1–165); Flt-1 selective variant; LK-VRB-2f; (described above in Example 10 above) or PlGF (R & D Systems)), or methylcellulose and aluminium sucralfate (100 ug) (controls) was inserted into the base of the pocket. After surgery, the eyes were coated with gentamicin ointment. At day 6, the animals were injected with high molecular weight FITC-dextran and euthanized to allow for visualization of the vasculature. Corneal whole mounts were made of the enucleated eyes and measurements of the neovascular area completed using computer-assisted image analysis (Image-Pro Plus).

As shown in FIG. 15A, the KDR-selective VEGF variant was as efficient as native VEGF in inducing corneal angiogenesis. While the Flt-1 selective VEGF variant occasionally induced marginal angiogenesis (FIG. 15A), analysis of the angiogenic surface areas in several animals showed that the Flt-1 selective VEGF variant was unable to stimulate angiogenesis over control levels. PlGF gave only a marginal response (FIG. 15B). Accordingly, it is presently believed that KDR, but not Flt-1, is capable of promoting angiogenesis in vivo.

The foregoing written description is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A variant of human VEGF comprising one or more non-conservative amino acid substitution(s) at residues 63 to 66 and one or more amino acid substitution(s) at residues 18, 21, 22, or 25, wherein the VEGF variant exhibits a higher KDR to Flt-1 binding ratio as compared with native VEGF.

2. The VEGF variant of claim 1, wherein at least one of the amino acid substitution(s) comprises M18E, Y21L, Q22R, or Y25S.

3. The VEGF variant of claim 1, wherein the amino acid substitutions comprise M18E, Y21L, Q22R, and Y25S.

4. An isolated nucleic acid sequence encoding the VEGF variant of claim 3.

5. An isolated nucleic acid sequence encoding the VEGF variant of claim 1.

6. A vector comprising the nucleic acid of claim 5.

7. A host cell comprising the vector of claim 6.

8. A composition comprising the VEGF variant of claim 1 and a carrier.

9. The composition of claim 8, wherein the carrier is a pharmaceutically acceptable carrier.

10. An assay for detecting KDR receptor, comprising contacting an isolated cell or tissue with a VEGF variant of claim 1 and assaying for binding of the VEGF variant to the cell or tissue.

11. A method for stimulating phosphorylation of a KDR receptor, comprising contacting a cell with a VEGF variant of claim 1 in amount effective to stimulate phosphorylation of the KDR receptor.

12. A method for stimulating MAP kinase activation, comprising contacting a cell with a VEGF variant of claim 1 amount effective to stimulate phosphorylation of MAP kinase.

13. A method for stimulating PLC-gamma activation, comprising contacting a cell with a VEGF variant of claim 1 in amount effective to stimulate phosphorylation of PLC-gamma.

14. A method for stimulating PI 3'-kinase activation, comprising contacting a cell with a VEGF variant of claim 1 in amount effective to stimulate phosphorylation of PI 3'-kinase.

15. A method for stimulating vasculogenesis or angiogenesis, comprising contacting endothelial cells expressing KDR receptor with an effective amount of a VEGF variant of claim 1.

16. A method for promoting the migration of endothelial cells, comprising contacting endothelial cells expressing KDR receptor with an effective amount of a VEGF variant of claim 1.

17. The VEGF variant of claim 1, wherein the amino acid substitutions further comprise a substitution at residue 17.

18. The VEGF variant of claim 1, wherein at least one of the amino acid substitution(s) comprises D63S, G65M, or L66R.

19. The VEGF variant of claim 18, wherein the amino acid substitutions comprise M18E, Y21L, Q22R, and Y25S.

20. The VEGF variant of claim 19, comprising amino acid substitutions M18E, Y12L, Q22R, Y25S, and D63S.

21. The VEGF variant of claim 19, comprising amino acid substitutions M18E, Y21L, Q22R, Y25S, and G65M.

22. The VEGF variant of claim 19, comprising amino acid substitutions M18E, Y21L, Q22R, Y25S, and L66R.

23. The VEGF variant of claim 19, comprising amino acid substitutions M18E, Y21L, Q22R, Y25S, D63S, and G65M.

24. The VEGF variant of claim 19, comprising amino acid substitutions M18E, Y21L, Q22R, Y25S, D63S, and L66R.

25. The VEGF variant of claim 19, comprising amino acid substitutions M18E, Y21L, Q22R, Y25S, G65M, and L66R.

26. The VEGF variant of claim 19, comprising amino acid substitutions M18E, Y21L, Q22R, Y25S, D63S, G65M, and L66R.

27. The VEGF variant of claim 1 wherein the amino acid substitutions comprise D63S, G65M, and L66R.

28. The VEGF variant of claim 27, wherein at least one of the amino acid substitution(s) comprise M18E, Y21L, Q22R, or Y25S.

29. The VEGF variant of claim 28, comprising amino acid substitutions.

30. An isolated nucleic acid sequence encoding the VEGF variant of claim 29.

31. An isolated nucleic acid sequence encoding the VEGF variant of claim 28.

32. The VEGF variant of claim 28, comprising amino acid substitutions Y21L, D63S, G65M, and L66R.

33. The VEGF variant of claim 28, comprising amino acid substitutions Q22R, D63S, G65M and L66R.

34. The VEGF variant of claim 28, comprising amino acid substitutions Y25S, D63S, G65M, and L66R.

35. The VEGF variant of claim 28, comprising amino acid substitutions M18E, Y21L, D63S, G65M, and L66R.

36. The VEGF variant of claim 28, comprising amino acid substitutions M18E, Q22R, D63S, G65M, and L66R.

37. The VEGF variant of claim 28, comprising amino acid substitutions M18E, Y25S, D63S, G65M, and L6R.

38. The VEGF variant of claim 28, comprising amino acid substitutions Y21L, Q22R, D63S, G65M, and L66R.

39. The VEGF variant of claim 28, comprising amino acid substitutions Y21L, Y25S, D63S, G65M, and L66R.

40. The VEGF variant of claim 28, comprising amino acid substitutions Q22R, Y25S, D63S, G65M, and L66R.

41. The VEGF variant of claim 28, comprising amino acid substitutions M18E, Y21L, Q22R, D63S, G65M, and L66R.

42. The VEGF variant of claim 28, comprising amino acid substitutions M18E, Q22R, Y25S, D63S, G65M, and L66R.

43. The VEGF variant of claim 28, comprising amino acid substitutions Y21L, Q22, Y25S, D63S, G65M, and L66R.

44. A variant of human VEGF comprising amino acid substitutions D63S, G65M, and L66R, wherein the variant exhibits a higher KDR to Flt-1 binding ratio as compared with native VEGF.

45. An isolated nucleic acid sequence encoding the VEGF variant of claim 44.

46. A vector comprising the nucleic acid of claim 45.

47. A variant of human VEGF comprising two or more amino acid substitutions at residues 17 to 25, wherein the VEGF variant exhibits a higher KDR to Flt-1 binding ratio as compared with native VEGF.

48. The VEGF variant of claim 47, wherein the amino acid substitutions comprise two or more amino acid substitutions at residues 18, 21, 22, or 25.

49. The VEGF variant of claim 47, wherein at least one of the amino acid substitution(s) comprise M18E, Y21L, Q22R, or Y25S.

50. The VEGF variant of claim 47, wherein the amino acid substitutions comprise M18E, Y21L, Q22R, and Y25S.

51. An isolated nucleic acid sequence encoding the VEGF variant of claim 50.

52. The VEGF variant of claim 47, wherein the amino acid substitutions comprise F17I, M18E, Y21F, Q22K, and Y25S.

53. The VEGF variant of claim 47, wherein the amino acid substitutions comprise F17I, M18E, Y21F, Q22E, and Y25I.

54. An isolated nucleic acid sequence encoding the VEGF variant of claim 47.

55. A variant of human VEGF, comprising:
(a) one or more amino acid substitution(s) at residues 17–25, and
(b) one or more amino acid substitution(s) at residues 63–66;
wherein amino acid residue 60 is cysteine, and the variant exhibits a hi her KDR to Fl-1 binding ratio as compared with native VEGF.

* * * * *

UNITED STATES PATENT AND TRADEMARK OFFICE
CERTIFICATE OF CORRECTION

PATENT NO. : 7,090,834 B1  
APPLICATION NO. : 09/546857  
DATED : August 15, 2006  
INVENTOR(S) : Cunningham et al.

Page 1 of 1

It is certified that error appears in the above-identified patent and that said Letters Patent is hereby corrected as shown below:

Title Page 2
OTHER PUBLICATIONS - Park reference, last line: "25646-15654" should read --25646-25654--

Column 6
Line 67 --variant ("Flt-sel"), and P1GF.-- should be inserted following "Flt-1 selective"

Column 39
Line 10 "L6R" should read --L66R--
Line 22 "Q22" should read --Q22R--

Column 40
Line 28 "hi her" should read --higher--

Signed and Sealed this

Ninth Day of January, 2007

JON W. DUDAS
*Director of the United States Patent and Trademark Office*